United States Patent
Lee et al.

(10) Patent No.: US 12,369,806 B2
(45) Date of Patent: Jul. 29, 2025

(54) ELECTRONIC DEVICE AND METHOD FOR PROVIDING BODY COMPONENT INFORMATION BY USING SAME

(71) Applicant: Samsung Electronics Co., Ltd., Gyeonggi-do (KR)

(72) Inventors: Wonseok Lee, Gyeonggi-do (KR); Jeongmin Park, Gyeonggi-do (KR)

(73) Assignee: Samsung Electronics Co., Ltd, Suwon-si (KR)

(*) Notice: Subject to any disclaimer, the term of this patent is extended or adjusted under 35 U.S.C. 154(b) by 342 days.

(21) Appl. No.: 17/880,004

(22) Filed: Aug. 3, 2022

(65) Prior Publication Data

US 2022/0369944 A1 Nov. 24, 2022

Related U.S. Application Data

(63) Continuation of application No. PCT/KR2021/001908, filed on Feb. 15, 2021.

(30) Foreign Application Priority Data

Feb. 12, 2020 (KR) .................. 10-2020-0016914

(51) Int. Cl.
*A61B 5/024* (2006.01)
*G06F 3/14* (2006.01)
*A61B 5/0537* (2021.01)

(52) U.S. Cl.
CPC ............ *A61B 5/02444* (2013.01); *G06F 3/14* (2013.01); *A61B 5/0537* (2013.01)

(58) Field of Classification Search
CPC ........ A61B 5/0244; A61B 5/0537; G06F 3/14
(Continued)

(56) References Cited

U.S. PATENT DOCUMENTS 6,256,532 B1 7/2001 Cha
6,400,983 B1 6/2002 Cha
(Continued)

FOREIGN PATENT DOCUMENTS

KR 2001-0011582 A 2/2001
KR 2001-0011583 A 2/2001
(Continued)

OTHER PUBLICATIONS

Korean Office Action dated Jan. 22, 2025.

*Primary Examiner* — Gabriel I Garcia
(74) *Attorney, Agent, or Firm* — Cha & Reiter, LLC

(57) ABSTRACT

An electronic device and method are disclosed. The electronic device includes a display, a first sensor, a communication module and a processor. The processor implements the method, including calculating a first impedance via the first biometric information, calculating a first body composition based on the first impedance, receiving second biometric information from an external electronic device, calculating a second impedance using the second biometric information, calculating a second body composition based the second impedance, calculating a total body composition based on at least one of the first impedance and the second impedance, calculating a third body composition for a third part of the body of the user, based on the total body composition, the first body composition, and the second body composition, and displaying at least one of the total body composition, the first body composition, and the second body composition, and the third body composition on the display.

19 Claims, 19 Drawing Sheets

(58) Field of Classification Search
USPC .......................................................... 382/128
See application file for complete search history.

(56) References Cited

U.S. PATENT DOCUMENTS

| | | | |
|---|---|---|---|
| 8,409,115 | B2 | 4/2013 | Kasahara |
| 2004/0059242 | A1* | 3/2004 | Masuo ................. A61B 5/6826 600/547 |
| 2016/0081581 | A1 | 3/2016 | Eom et al. |
| 2016/0198977 | A1 | 7/2016 | Eom et al. |
| 2016/0249857 | A1* | 9/2016 | Choi .................... A61B 5/4872 600/547 |
| 2017/0188944 | A1 | 7/2017 | Banet et al. |
| 2018/0235507 | A1* | 8/2018 | Kim ..................... A61B 5/0537 |

FOREIGN PATENT DOCUMENTS

| | | | |
|---|---|---|---|
| KR | 10-2001-0019513 A | 3/2001 | |
| KR | 2001-0017248 A | 3/2001 | |
| KR | 10-2004-0001611 A | 1/2004 | |
| KR | 10-2016-0035853 A | 4/2016 | |
| KR | 10-2016-0065330 A | 6/2016 | |
| KR | 10-2016-0086715 A | 7/2016 | |
| KR | 10-1689553 B1 | 12/2016 | |

\* cited by examiner

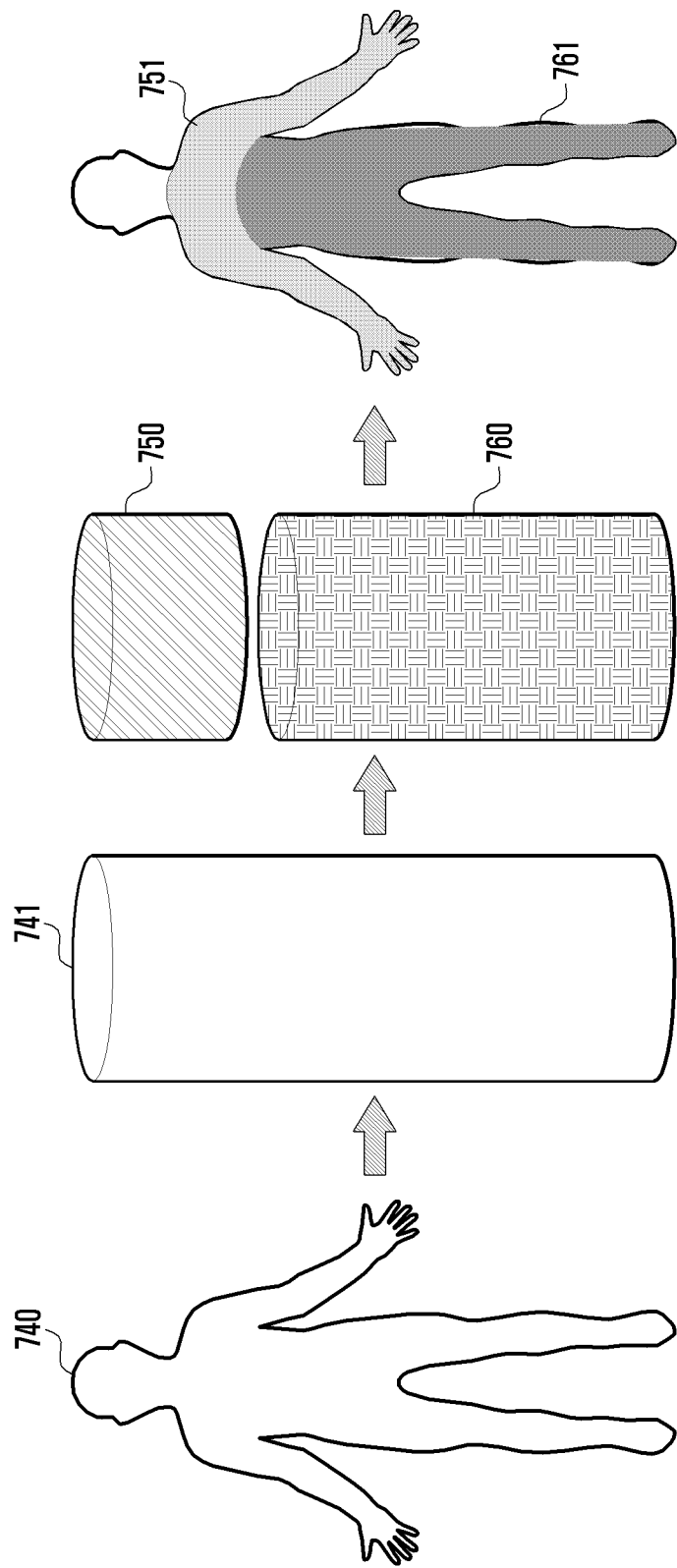

ELECTRONIC DEVICE AND METHOD FOR PROVIDING BODY COMPONENT INFORMATION BY USING SAME

CROSS-REFERENCE TO RELATED APPLICATION(S)

This application is a continuation of International Application No. PCT/KR2021/001908, which was filed on Feb. 15, 2021, and claims priority to Korean Patent Application No. 10-2020-0016914, filed on Feb. 12, 2020, in the Korean Intellectual Property Office, the disclosures of which are incorporated by reference herein their entirety.

BACKGROUND

Technical Field

The present disclosure relates to detection of user biometrics and, more particular, to biometric detection of user body composition using one or more communicably interlinked electronic devices.

Description of Related Art

Body composition refers to biological components of the body and is often expressed in percentages. Body composition may thus indicate percentages of fat, muscle, and water within the body. Estimates of health often utilize this data for calculations and estimates.

Bioelectrical impedance analysis (BIA) is one example method of measuring body composition. The BIA method is based on the differences in penetration of an electric signal into a body part. A part containing more water may have a lower electrical resistance compared to a part containing less water. By introducing a current flow into some sections of the body and analyzing a resultant voltage in the corresponding sections, body composition ratios can be acquired, when used in tandem with information such as resistance, gender, height, age, and weight.

SUMMARY

The BIA method may be performed through a dedicated device. However, oftentimes, such devices may be bulky and cumbersome, rendering it difficult to measure body composition. In order to solve this problem, the BIA method may be implemented on simpler devices capable of introducing current flow, and measuring a current in some body parts. While some such devices have been released, the measurements are often performed on limited portions of a body, and thus measurements of body composition for each body part are impeded.

Certain embodiments of the disclosure provide an electronic device and a method for measuring body composition information for each body part, facilitating convenient reception of body composition information through an electronic device which is easily carried and used.

An electronic device according to certain embodiments in the disclosure includes a display; a first sensor configured to measure first biometric information for a first part of a body of a user; a communication module; and a processor operatively connected to the display, the first sensor, and the communication module, wherein the processor is configured to: calculate a first impedance via the first biometric information, and calculate a first body composition based on the first impedance, receive second biometric information from an external electronic device including a second sensor that measured the second biometric information for a second part of the body of the user, via the communication module, calculate a second impedance using the second biometric information, and calculate a second body composition based the second impedance, calculate a total body composition, based on at least one of the first impedance and the second impedance, calculate a third body composition for a third part of the body of the user, based on the total body composition, the first body composition, and the second body composition, and display at least one of the total body composition, the first body composition, and the second body composition, and the third body composition on the display.

A method of providing body composition information of a user through an electronic device according to certain embodiments in the disclosure includes measuring first biometric information for a first part of a body of a user via a first sensor; calculating, via a processor, a first impedance using the first biometric information, and calculating a first body composition based on the first impedance; receiving, via communication circuitry, second biometric information from an external electronic device including a second sensor measuring second biometric information for a second part of the body of the user; calculating a second impedance using the second biometric information, and calculating a second body composition based on the second impedance; calculating a total body composition, based on at least one of the first impedance and the second impedance; calculating a third body composition for a third part of the body of the user, based on the total body composition, the first body composition, and the second body composition; and displaying at least one of the total body composition, the first body composition, the second body composition, and the third body composition on a display.

An electronic device according to certain embodiments in the disclosure includes a display; a first sensor configured to measure first biometric information from both arms of a user; a communication module; and a processor operatively connected to the display, the first sensor, and the communication module, wherein the processor is configured to: identify whether the electronic device is communicably linked to an external electronic device including a second sensor for measuring second biometric information from both legs of the user, selectively activate an operational scenario from among a plurality of scenarios, based on whether the electronic devices are communicably linked, wherein a first scenario of the plurality of scenarios causes the processor to: calculate a first impedance by using the first biometric information, calculate a first body composition, based on the first impedance, receive second biometric information from the external electronic device through the communication module, calculate a second impedance by using the second biometric information, calculate a second body composition from the second impedance, calculate a total body composition, based on at least one of the first impedance and the second impedance, calculate a third body composition for a third part of a body of the user, based on the total body composition, the first body composition, and the second body composition, and display at least one of the total body composition, the first body composition, the second body composition, and the third body composition on the display, and wherein a second scenario of the plurality of scenarios causes the processor to: calculate the first impedance by using the first biometric information, calculate the first body composition, based on the first impedance, calculate the total body impedance and the total body composition from the first impedance, and display at least one of the total body composition and the first body composition on the display.

According to certain embodiments of the disclosure, body composition information may be more conveniently generated and reported for users, and furthermore, the information may be more granular with respect to each body part. Thus, the disclosure may aid in detecting and managing a user's body state.

BRIEF DESCRIPTION OF THE DRAWINGS

In connection with a description of drawings, the same or similar reference numerals may be used for the same or similar elements.

FIG. 7D illustrates a method of providing body composition information for each body part of the user according to certain embodiments of the disclosure;

DETAILED DESCRIPTION

Figure 1:
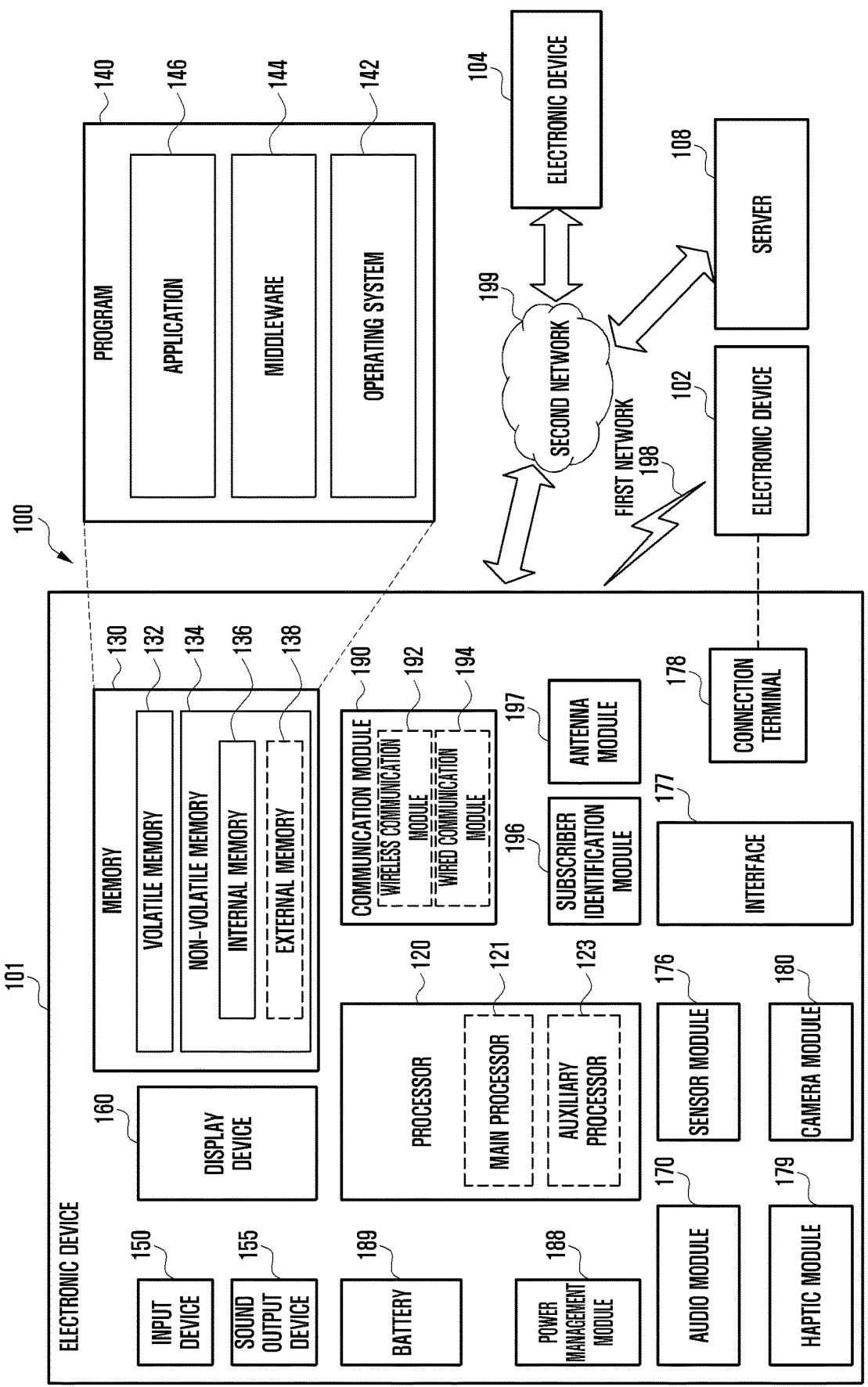
FIG. 1 is a block diagram illustrating an electronic device within a network environment according to certain embodiments.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134, which in turn may include internal memory 136 and external memory 138. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors (e.g., and communication circuitry) that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element implemented using a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2A:
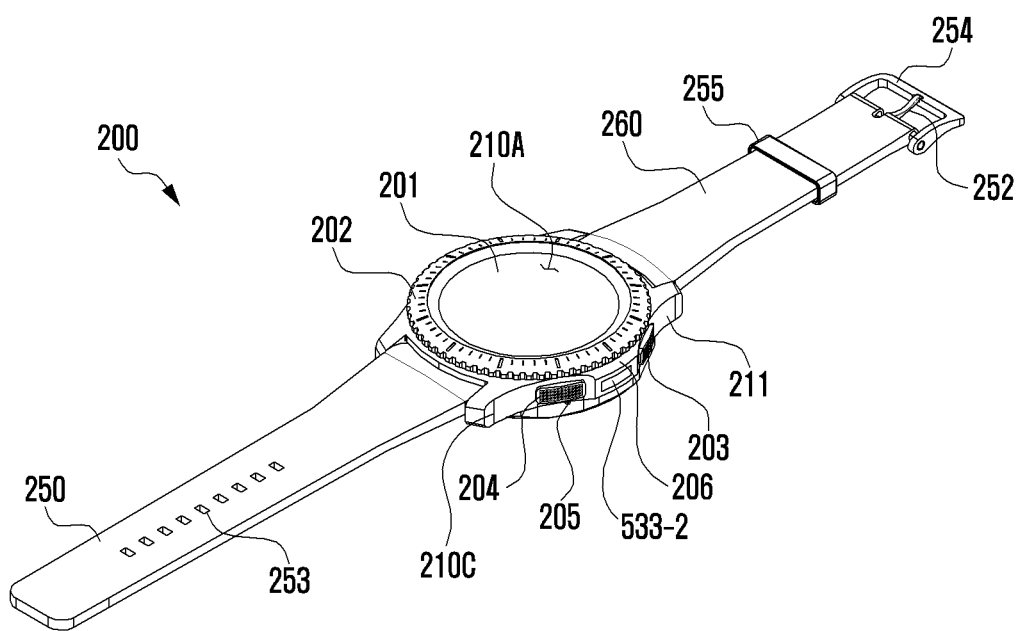
FIG. 2A is a front perspective view of a mobile electronic device according to certain embodiments of the disclosure.
Figure 2B:
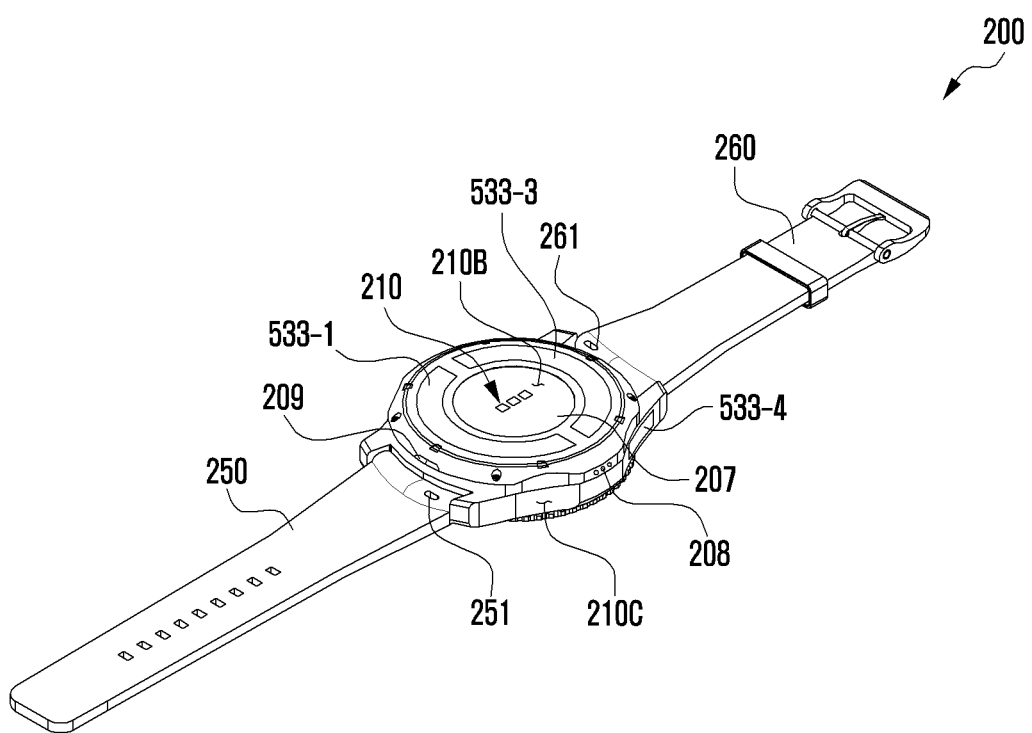
FIG. 2B is a rear perspective view of the electronic device in FIG. 2A according to certain embodiments of the disclosure.

Referring to FIG. 2A and FIG. 2B, the electronic device 200 according to an embodiment may include: a housing 210 including a first surface (or front surface) 210A, a second surface (or rear surface) 210B, and a side surface 210C surrounding the space between the first surface 210A and the second surface 210B; and clamping members 250 and 260 connected to at least a part of the housing 210 and configured such that the electronic device 200 is clamped to a part of the user's body (such as, for example, the wrist, ankle, or the like) in an attachable/detachable manner. In another embodiment (not illustrated), the housing may refer to a structure forming at least some of the first surface 210A, the second surface 210B, and the side surface 210C in FIG. 2A. According to an embodiment, the first surface 210A may be formed by a front plate 201, at least a part of which is substantially transparent (such as, for example, a glass plate including various coating layers, or a polymer plate). The second surface 210B may be formed by a rear plate 207 which is substantially opaque. The rear plate 207 may be made of, for example, coated or colored glass, ceramic, polymer, metal (such as, for example, aluminum, stainless steel (STS), or magnesium), or a combination of at least two of the above materials. The side surface 210C may be formed by a side bezel structure (also referred to as "side member") 206, which is coupled to the front plate 201 and the rear plate 207, and which includes a metal and/or a polymer. In some embodiments, the rear plate 207 and the side bezel structure 206 may be formed integrally and made of the same material (such as, for example, a metal material such as aluminum). The clamping members 250 and 260 may be made of various materials and in various types. The clamping members 250 and 260 may be made of a woven material, leather, rubber, urethane, metal, ceramic, or a combination of at least two of the above materials in an integrated type, and may be formed such that multiple unit links can move with regard to each other.

According to an embodiment, the electronic device 200 may include at least one of a display 220 (see FIG. 3), audio modules 205 and 208, a sensor module 211, key input devices 202, 203, and 204, and a connector hole 209. In some embodiments, at least one of the components of the electronic device 200 (such as, for example, the key input devices 202, 203, and 204, the connector hole 209, or the sensor module 211) may be omitted, or other components may be further included.

The display 220 may be exposed through a corresponding part of the front plate 201, for example. The display 220 may have one of various shapes, such as a circle, an ellipse, or a polygon, which corresponds to that of the front plate 201. The display 220 may be coupled to or disposed adjacent to a touch sensing circuit, a pressure sensor capable of sensing the intensity (pressure) of a touch, and/or a fingerprint sensor.

The audio modules 205 and 208 may include a microphone hole and a speaker hole. The microphone hole may have a microphone disposed therein so as to acquire an external sound, and may have multiple microphones disposed therein so as to sense the direction of the sound, in some embodiments. The speaker hole may be used as an external speaker and a telephone speech receiver.

The sensor module 211 may produce an electric signal or a data value corresponding to the operating state inside the electronic device 200 or the environmental state outside the same. The sensor module 211 may include a biometric sensor module 211 (such as, for example, an HRM sensor) disposed on the second surface 210B of the housing 210, for example. The electronic device 200 may further include a sensor module (not illustrated), for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 202, 203, and 204 may include a wheel key 202 disposed on the first surface 210A of the housing 210 to be able to rotate in at least one direction and/or side key buttons 203 and 205 disposed on the side surface 201C of the housing 210. The wheel key 202 may have a shape corresponding to that of the front plate 201. In another embodiment, the electronic device 200 may not include some or all of the above-mentioned key input devices 202, 203, and 204, and the key input devices 202, 203, and 204 that are not included may be implemented as other types (such as, for example, soft keys) on the display 220. The connector hole 209 may include other connector holes (not illustrated) capable of containing a connector (such as, for example, USB connector) for transmitting/receiving power and/or data to/from an external electronic device, and capable of containing a connector for transmitting/receiving audio signals to/from an external electronic device. The electronic device 200 may further include a connector cover (not illustrated) covering at least a part of the connector hole 209, for example, and preventing external foreign substances from entering the connector hole.

The clamping members 250 and 260 may be clamped to at least a partial region of the housing 210 in an attachable/detachable manner by using locking members 251 and 261. The clamping members 250 and 260 may include at least one of a fixing member 252, a fixing-member fastening hole 253, a band guide member 254, and a band-fixing ring 255.

The fixing member 252 may be configured to fix the housing 210 and the clamping members 250 and 260 to a part of the user's body (such as, for example, the wrist, ankle, or the like). The fixing-member fastening hole 253 may correspond to the fixing member 252 such that the housing 210 and the clamping members 250 and 260 are fixed to a part of the user's body. The band guide member 254 may be configured to limit the range of movement of the fixing member 252 when the fixing member 252 is fastened to the fixing-member fastening hole 253, thereby enabling the clamping members 250 and 260 to be forced against and clamped to a part of the user's body. The band-fixing ring 255 may limit the range of movement of the clamping members 250 and 260 while the fixing member 252 and the fixing-member fastening hole 253 are fastened.

Figure 3:
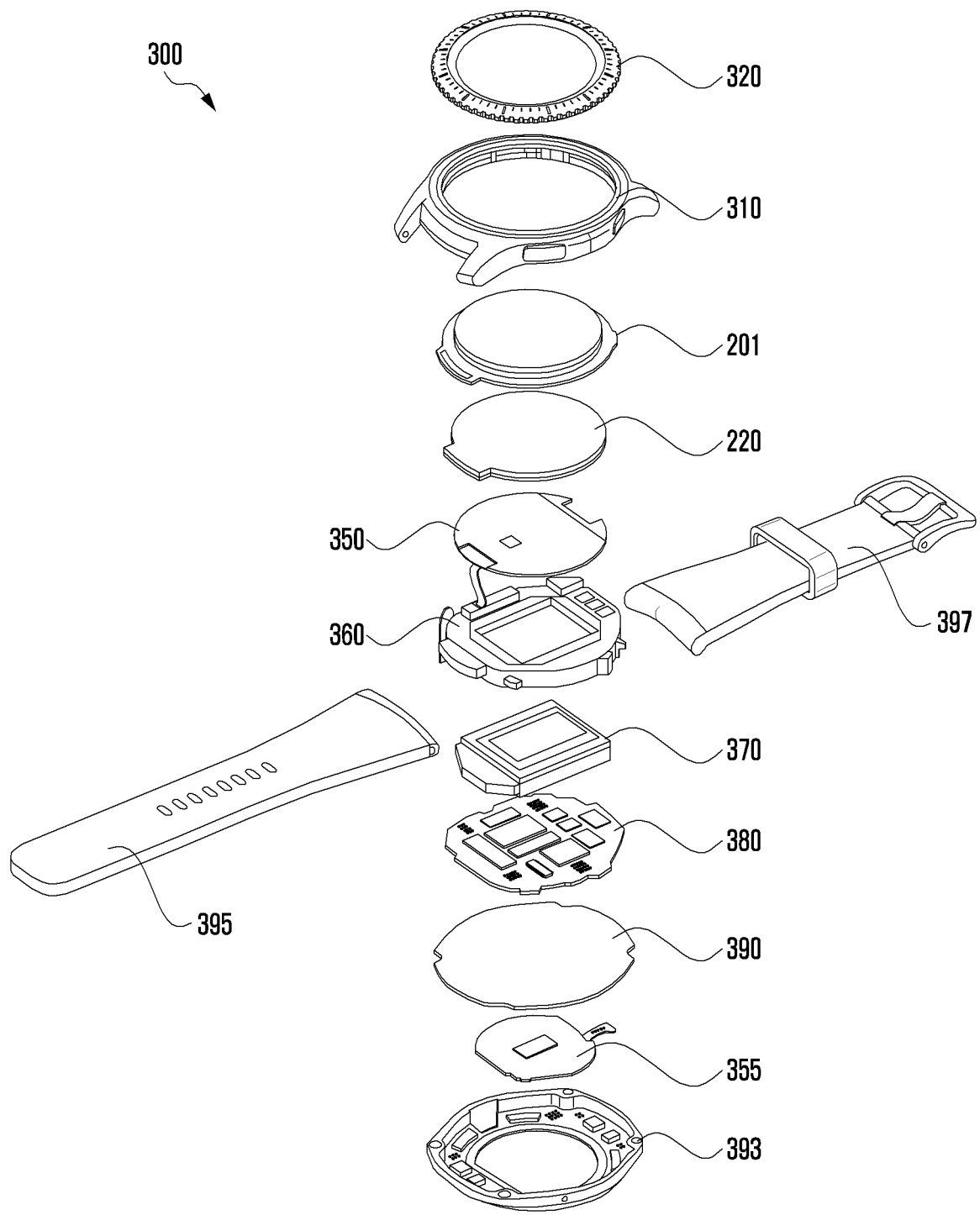
FIG. 3 is an exploded perspective view of the electronic device in FIG. 2A according to certain embodiments of the disclosure.

Referring to FIG. 3, the electronic device 300 may include a side bezel structure 310, a wheel key 320, a front plate 201, a display 220, a first antenna 350, a second antenna 355, a support member 360 (such as, for example, a bracket), a battery 370, a printed circuit board 380, a sealing member 390, a rear plate 393, and clamping members 395 and 397. At least one component of the electronic device 300 may be identical or similar to at least one component of the electronic device 200 in FIG. 2A or FIG. 2B, and a repeated description thereof will thus be omitted herein. The support member 360 may be disposed inside the electronic device 300 and connected to the side bezel structure 310, or may be formed integrally with the side bezel structure 310. The support member 360 may be made of a metal material and/or a nonmetal (such as, for example, polymer) material, for example. The display 220 may be coupled to one surface of the support member 360, and the printed circuit board 380 may be coupled to the other surface thereof. A processor, a memory, and/or an interface may be mounted on the printed circuit board 380. The processor may include at least one of a central processing device, an application processor, a graphic processing unit (GPU), an application processor signal processing unit, or a communication processor, for example.

The memory may include, for example, a volatile memory or a nonvolatile memory. The interface may include, for example, a high-definition multimedia interface (HDMI), a universal serial bus (USB) interface, an SD card interface, and/or an audio interface. The interface may connect the electronic device 300 to an external electronic device electrically or physically, for example, and may include a USB connector, an SD card/MMC connector, or an audio connector.

The battery 370, which is a device for supplying power to at least one component of the electronic device 300, may include a primary battery that is not rechargeable, a secondary battery that is rechargeable, or a fuel cell, for example. At least a part of the battery 370 may be disposed on substantially the same plane as the printed circuit board 380, for example. The battery 370 may be integrally disposed inside the electronic device 200, or may be disposed such that the same can be attached to/detached from the electronic device 200.

The first antenna 350 may be disposed between the display 220 and the support member 360. The first antenna 350 may include, for example, a near-field communication (NFC) antenna, a wireless charging antenna, and/or a magnetic secure transmission (MST) antenna. The first antenna 350 may conduct short-range communication with an external device, for example, may wirelessly transmit/receive power utilized for charging, and may emit a magnetism-based signal including a short-range communication signal or payment data. In another embodiment, an antenna structure may be formed by a part or a combination of the side bezel structure 310 and/or the support member 360.

The second antenna 355 may be disposed between the circuit board 380 and the rear plate 393. The second antenna 355 may include, for example, a near-field communication (NFC) antenna, a wireless charging antenna, and/or a magnetic secure transmission (MST) antenna. The second antenna 355 may conduct short-range communication with an external device, for example, may wirelessly transmit/receive power utilized for charging, and may emit a magnetism-based signal including a short-range communication signal or payment data. In another embodiment, an antenna structure may be formed by a part or a combination of the side bezel structure 310 and/or the rear plate 393.

The sealing member 390 may be positioned between the side bezel structure 310 and the rear plate 393. The sealing member 390 may be configured to prevent external moisture and foreign substances from entering the space surrounded by the side bezel structure 310 and the rear plate 393.

Figure 4:
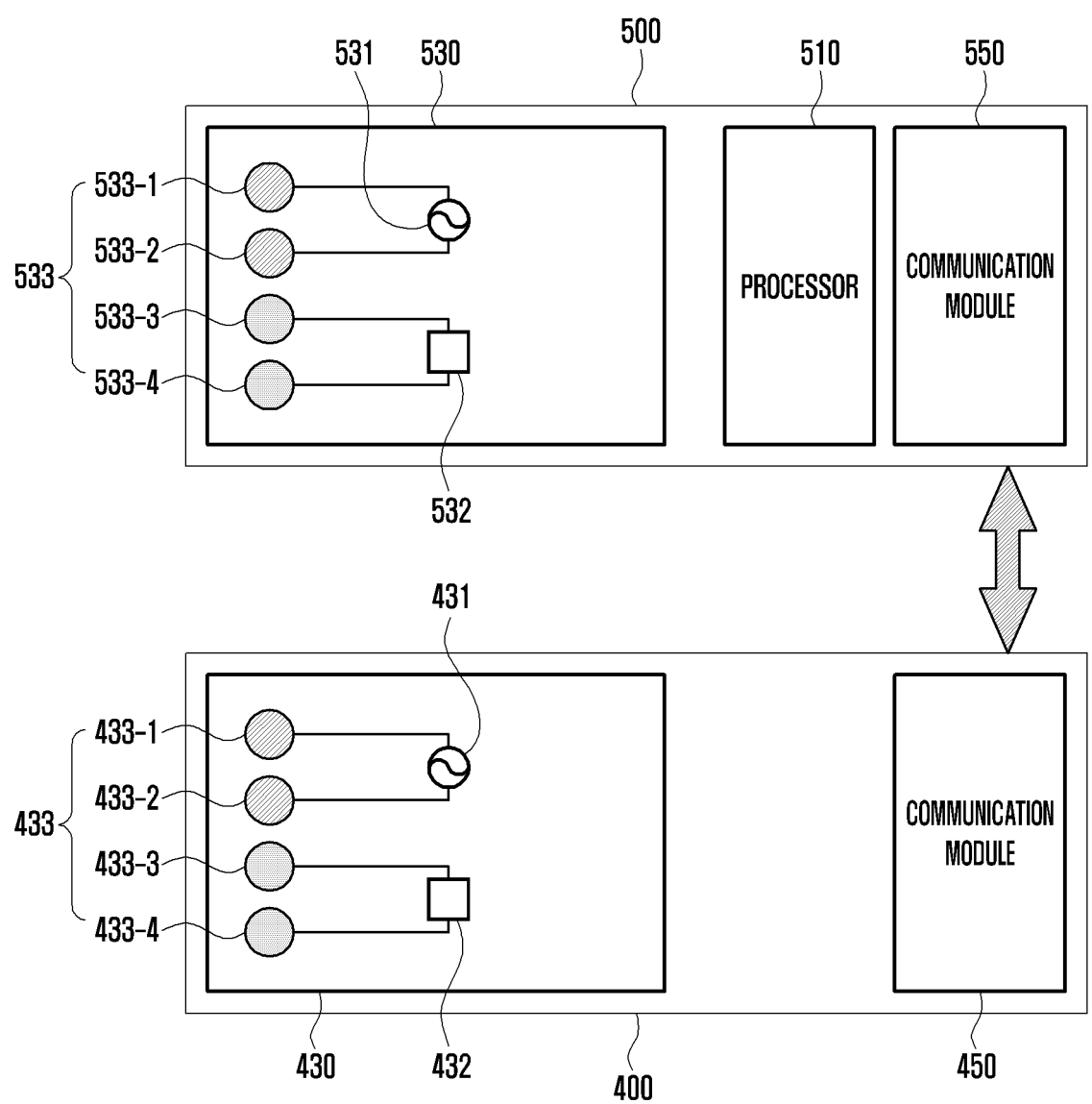
FIG. 4 is a block diagram of an electronic device and an external electronic device according to certain embodiments of the disclosure.
Figure 5:
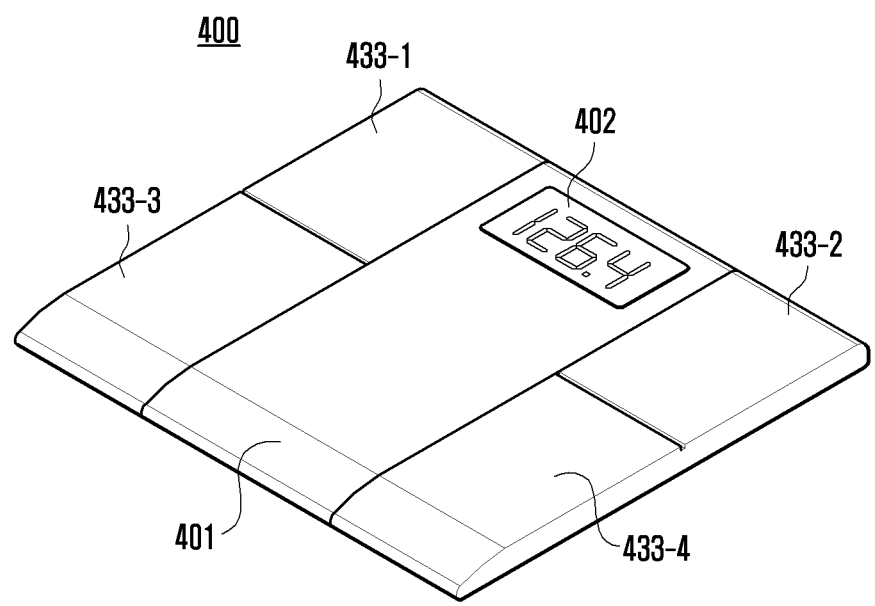
FIG. 5 is a perspective view of an external electronic device according to certain embodiments of the disclosure.

FIG. 4 is a block diagram illustrating an electronic device and an external electronic device according to certain embodiments of the disclosure, and FIG. 5 is a perspective view of the external electronic device according to certain embodiments of the disclosure.

An electronic device 500 (such as, for example, the electronic device 101 of FIG. 1 or the electronic device 200 of FIG. 2A) according to certain embodiments of the disclosure may include at least one of a display (such as, for example, the display device 160 of FIG. 1 or the display 220 of FIG. 3), a communication module 550 (such as, for example, the communication module 190 of FIG. 1), a processor 510 (such as, for example, the processor 120 of FIG. 1), or a first sensor 530.

Hereinafter, it is described that the electronic device is a wearable electronic device (such as, for example, the electronic device 200 of FIG. 2A), but the electronic device according to the disclosure of the disclosure is not limited to such a type of electronic device. For example, the electronic device may include at least one of a smartphone, a tablet personal computer (PC), a mobile phone, a video phone, an e-book reader, a desktop PC, a laptop PC, a netbook computer, a workstation, a server, a personal digital assistant (PDA), a portable multimedia player (PMP), an MP3 player, a mobile medical device, a camera, a wearable device (such as, for example, smart glasses, a head-mounted-device (HMD)), electronic clothes, an electronic bracelet, an electronic necklace, an electronic appcessory, an electronic tattoo, or a smart mirror. Various other types of electronic devices may be the electronic devices according to certain embodiments of the disclosure.

Body composition information described below may be information related to components (composition) in the body. For example, body composition may be components making up the weight such as water, protein, minerals, and body fat. Through body composition analysis, it is possible to accurately identify body fat, muscles, and a change in body fat percentage. The body composition analysis may be variously used for personal training (PT), medical treatment, and health promotion.

"Measurement" described hereinafter may be an operation of detecting an electric signal or a specific value in order to acquire specific information by a sensor. "Calculation" described hereinafter may be an operation of performing operations on the basis of information acquired or stored through various methods by a processor (such as, for example, a processor 510 of FIG. 4).

According to certain embodiments, the first sensor 530 of the electronic device 500 may be a sensor for measuring a user's biometric signal. For example, the first sensor 530 may be a sensor including a plurality of electrodes (such as, for example, a first electrode 533-1, a second electrode 533-2, a third electrode 533-3, and a fourth electrode 533-4) for bioelectrical impedance analysis (BIA). BIA is a method of analyzing body composition that leverages differences in a flowing electric signal within a body, according to a content level of water within body components.

According to certain embodiments, the first sensor 530 may include at least one of a plurality of electrodes 533 (the first electrode 533-1, the second electrode 533-2, the third electrode 533-3, and the fourth electrode 533-4), a first alternating current generator 531, or a first voltage measurer 532. The first electrode 533-1 and the third electrode 533-3 may be disposed in some areas of the housing (such as, for example, housing 210 of FIG. 2B) of the electronic device. For example, as illustrated in FIG. 2B, the first electrode 533-1 and the third electrode 533-3 may be disposed in some areas of the rear surface (such as, for example, the second surface 210B of FIG. 2B) facing the display. The second electrode 533-2 and the fourth electrode 533-4 may be disposed in some areas of the electronic device. For example, as illustrated in FIGS. 2A and 2B, the second electrode 533-2 and the fourth electrode 533-4 may be disposed in some areas of the side surface (such as, for example, the side surface 210C of FIGS. 2A and 2B) of the housing of the electronic device. According to certain embodiments, the second electrode 533-2 and the fourth electrode 533-4 may be disposed in parts facing each other on the side surface of the housing. The first electrode 533-1 and the second electrode 533-2 may be electrically connected to the first alternating current generator 531. The third electrode 533-3 and the fourth electrode 533-4 may be electrically connected to the first voltage measurer 532.

According to certain embodiments, the communication module 550 of the electronic device may transmit or receive information to or from the communication module 450 of the external electronic device 400 through various types of wireless networks. For example, the communication module 550 of the electronic device may communicate with the communication module 450 of the external electronic device 400 through a short-range communication network such as Bluetooth, WiFi direct, or infrared data association (IrDA) or a long-range communication network such as a cellular network, Internet, or a computer network (such as, for example, LAN or WAN).

According to certain embodiments, the external electronic device 400 may include at least one of a footholder 401, a display 402, a communication module 450, or a second sensor 430. The external electronic device 400 may be, for example, a scale capable of weighing a user's weight.

According to certain embodiments, the footholder 401 may correspond to a part on which the user steps. The footholder 401 may be a part to which the user's load is applied. The external electronic device 400 may calculate the user's weight by using the user's load applied through the footholder 401.

According to certain embodiments, the display 402 may be disposed in some areas of the footholder 401. The display 402 may display information such as the user's weight obtained through the external electronic device 400.

According to certain embodiments, the second sensor 430 may be a sensor including a plurality of electrodes for the BIA. The second sensor 430 may include at least one of a plurality of electrodes 433 (a fifth electrode 433-1, a sixth electrode 433-2, a seventh electrode 433-3, and an eighth electrode 433-4), a second alternating current generator 431, or a second voltage measurer 432. The fifth electrode 433-1, the sixth electrode 433-2, the seventh electrode 433-3, and the eighth electrode 433-4 may be disposed in some areas of the footholder 401 of the external electronic device 400 to which the user applies the weight. The fifth electrode 433-1 and the seventh electrode 433-3 may be disposed in some areas of the footholder 401 so that they come into contact with one of two soles of the user. The sixth electrode 433-2 and the eighth electrode 433-4 may be disposed in some areas of the footholder 401 so that they come into contact with the other one of the two soles of the user. For example, the fifth electrode 433-1 and the seventh electrode 433-3 may be disposed in a left area of the footholder 401 and the sixth electrode 433-2 and the eighth electrode 433-4 may be disposed in a right area of the footholder 401, as seen in FIG. 5.

According to certain embodiments, the communication module 450 of the external electronic device 400 may transmit or receive information to or from the communication module 550 of the electronic device 500 (such as, for example, the electronic device 101 of FIG. 1 or the electronic device 200 of FIG. 2A) through various types of wireless network. For example, the communication module 450 of the external electronic device 400 may communicate with the communication module 550 of the electronic device 500 through a short-range communication network such as Bluetooth, WiFi direct, or infrared data association (IrDA) or a long-range communication network such as a cellular network, Internet, or a computer network (such as, for example, LAN or WAN).

Figure 6A:
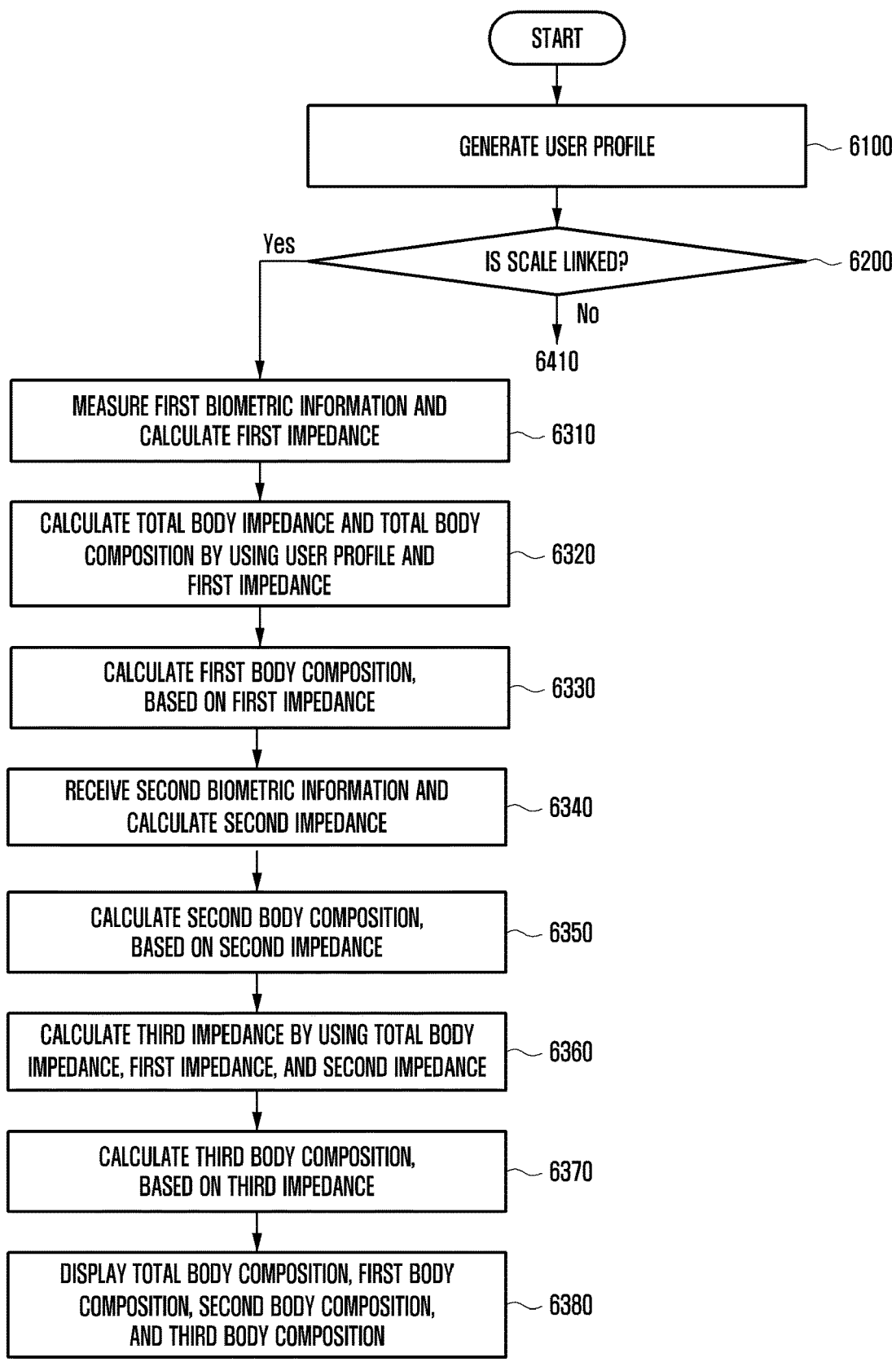
FIG. 6A is a flowchart illustrating a first scenario for providing a user's body composition information according to certain embodiments of the disclosure.
Figure 7A:
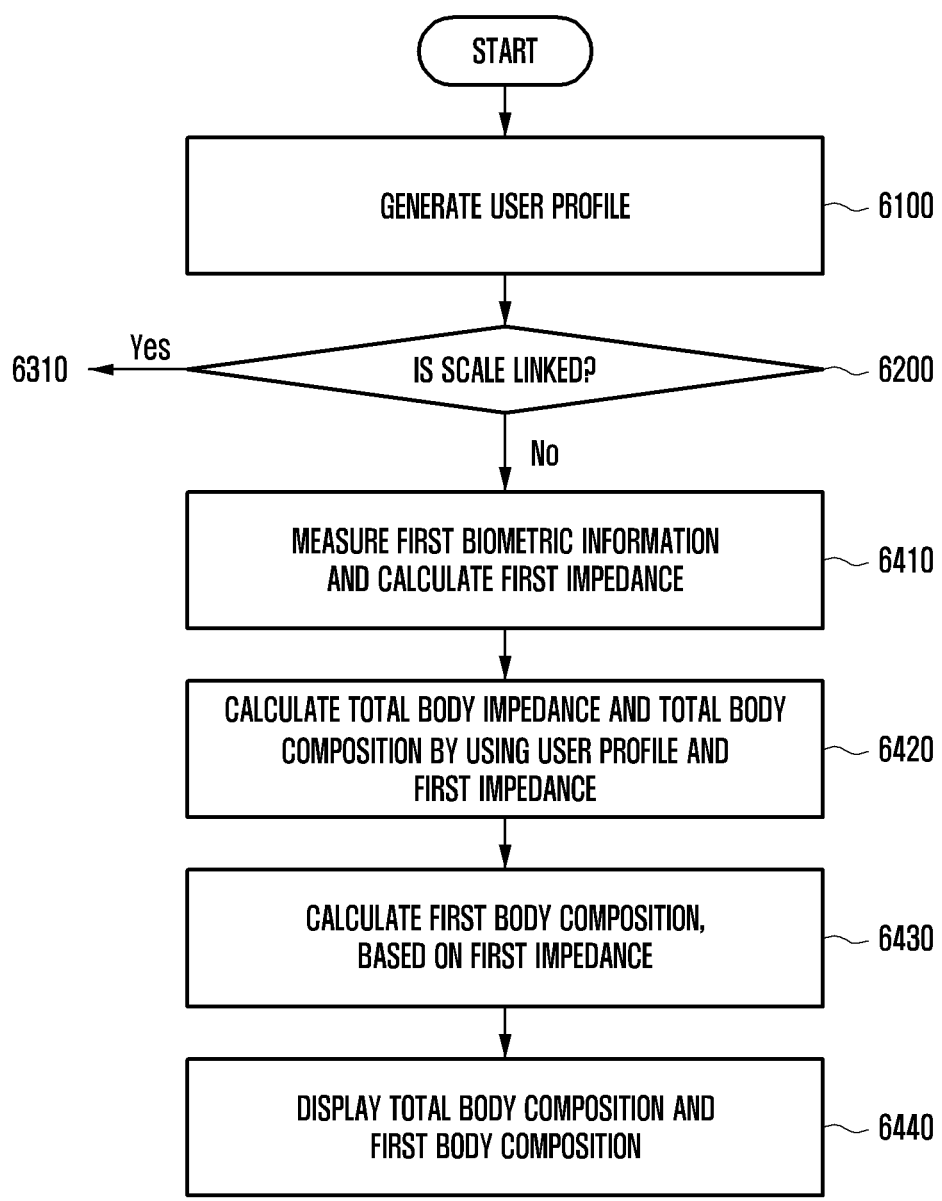
FIG. 7A is a flowchart illustrating a second scenario for providing a user's body composition information according to certain embodiments of the disclosure.

FIG. 6A is a flowchart illustrating a first scenario for providing a user's body composition information according to certain embodiments of the disclosure, and FIG. 7A is a flowchart illustrating a second scenario for providing a user's body composition information according to certain embodiments of the disclosure. The flowchart is only one example, and orders of the respective operations may be variously changed.

According to certain embodiments, a processor (such as, for example, the processor 510 of FIG. 4) of an electronic device (such as, for example, the electronic device 500 of FIG. 4) may display an interface capable of receiving an input for completing a user profile on the display of the electronic device, so that the user can input into the user profile information including his/her own weight, age, gender, and height into the electronic device. The electronic device may generate a user profile on the basis of one or more user inputs in operation 6100. When an external electronic device (such as, for example, the scale-based external electronic device 400 of FIG. 5) is able to provide the user's weight simultaneously while the electronic device receives inputting of the user profile information from the user, the electronic device may receive the user's weight as measured by the external electronic device and store the same in the user profile. According to certain embodiments, and alternatively, the electronic device may receive the user profile from a server which stores the user profile and generate the user profile.

According to certain embodiments, the processor may identify whether the external electronic device is communicably linked to the electronic device in operation 6200. Whether the external electronic device is linked to the electronic device may be identified in various ways.

For example, the processor of the electronic device may identify whether the external electronic device can be connected to the electronic device through a communication module (such as, for example, the communication module 550 of FIG. 4). When the electronic device is being connected to the external electronic device, the processor may determine that the external electronic device is linked to the electronic device. In another example, the processor may identify whether the external electronic device is linked to the electronic device on the basis of a user input. When the user desires to link the external electronic device with the electronic device, the processor may connect the electronic device with the external electronic device through the communication module. When the electronic device cannot be connected to the external electronic device, the processor may inform the user that they cannot be connected to each other through various notification means such as a display or a vibration-generating device.

According to certain embodiments, the processor may determine the operation of the electronic device through various scenarios according to whether the external electronic device and the electronic device are linked to each other. Hereinafter, the state in which the external electronic device is linked to the electronic device is referred to as a first scenario and the state in which the external electronic device is not linked to the electronic device is referred to as a second scenario.

Figure 6B:
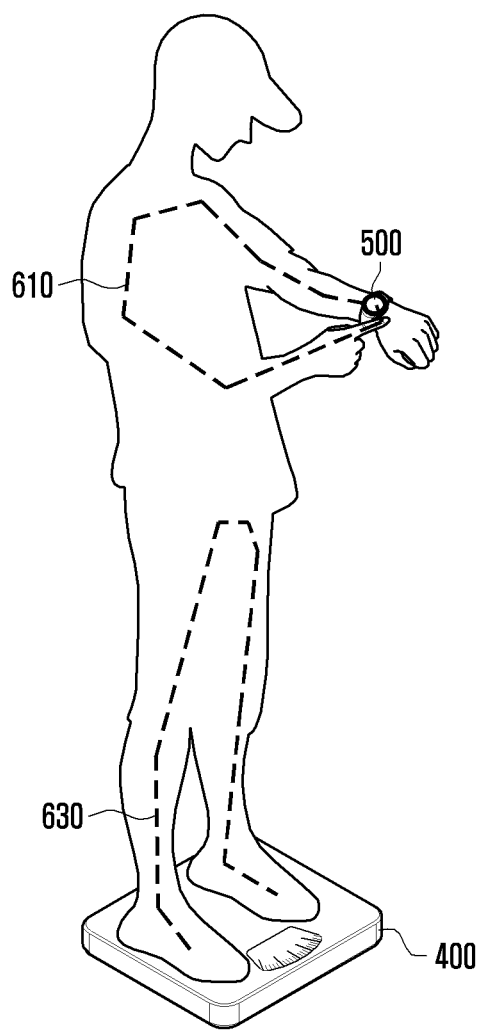
FIG. 6B illustrates an electronic device and an external electronic device to generate a plurality of electric loops in a user's body according to certain embodiments of the disclosure.

First, the first scenario is described with reference to FIGS. 6A to 6F. FIG. 6B illustrates an electronic device and an external electronic device to generate a plurality of electric loops in a user's body according to certain embodiments of the disclosure, FIG. 6C illustrates that the electronic device generates electric loops in a user's body part according to certain embodiments of the disclosure, FIG. 6D illustrates that the external electronic device generates electric loops in a user's body part according to certain embodiments of the disclosure, FIG. 6E illustrates a method of providing body composition information for each body part of the user according to certain embodiments of the disclosure, and FIG. 6F illustrates body composition information for each body part of the user, displayed on the display according to certain embodiments of the disclosure.

Body composition can be analyzed using bioelectrical impedance analysis (BIA). The BIA may be an analysis method of applying an alternating current to a human body, measuring impedance, and obtaining body composition on the basis of the measured impedance. In general, bioimpedance may be inversely proportional to the amount of water. The amount of water may be calculated by measuring impedance. It may be assumed that the total water content is consistently maintained as about 73% of fat-free mass (FFM) in the case of health adults, as 80% in the case of newborn babies, and as 75% in the case of 10 year old children. Fat-free mass may be calculated on the basis of the amount of water calculated using impedance. The amount of fat may be calculated using the weight and the fat-free mass. Component ratios of the fat-free mass may be known through statistical documents. On the basis of the component ratios of the fat-free mass, muscles and minerals may be obtained from the fat-free mass.

The first sensor 530 of the electronic device 500 may measure first biometric information in operation 6310. Referring to FIG. 6B, a first sensor (such as, for example, the first sensor 530 of FIG. 5) of the electronic device 500 may be in contact with a first part (such as, for example, an upper body) of the user's body to generate a first loop 610 (e.g., an electrically closed loop), and a second sensor (such as, for example, the second sensor 430 of FIG. 5) of the external electronic device 400 is in contact with a second part (such as, for example, a lower body) of the user's body to generate a second loop 630. First biometric information may be information utilized for calculating first impedance (such as, for example, first impedance 650 of FIG. 6E). For example, the first biometric information may relate to an alternating current, an alternating voltage, and an alternating frequency.

Figure 6C:
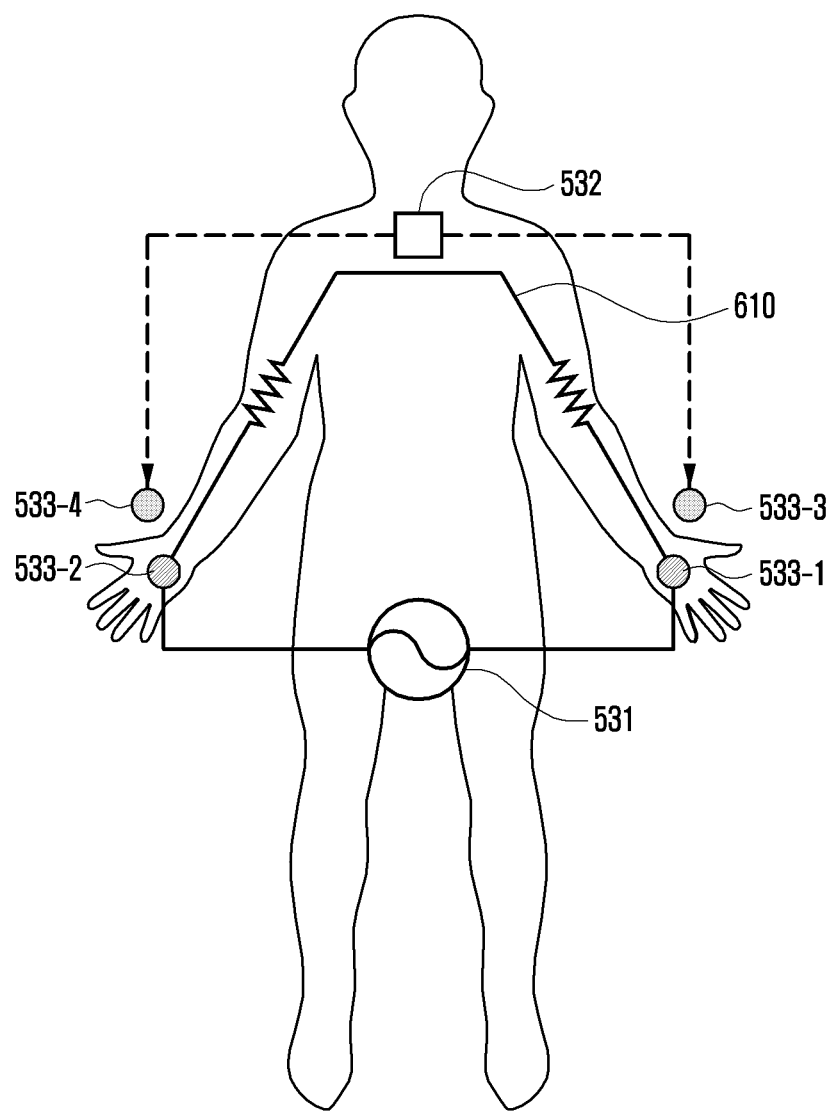
FIG. 6C illustrates that an electronic device generates electric loops in a user's body part according to certain embodiments of the disclosure.
Figure 6D:
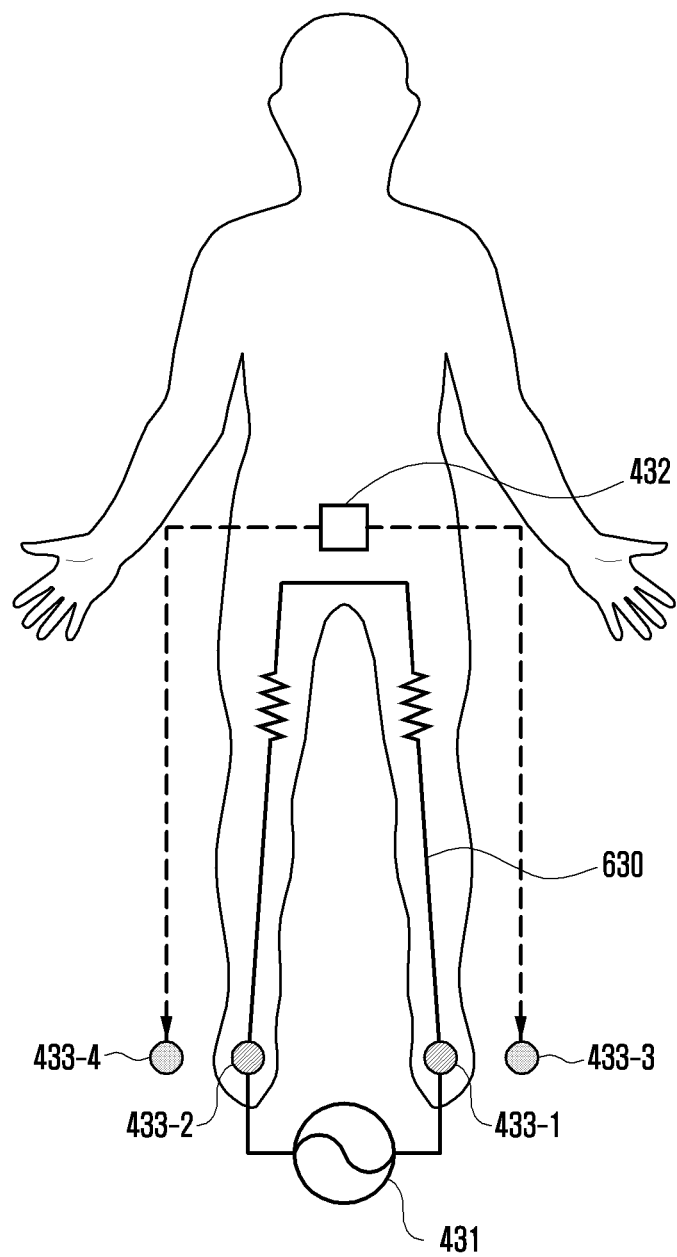
FIG. 6D illustrates that an external electronic device generates electric loops in a user's body part according to certain embodiments of the disclosure.
Figure 6E:
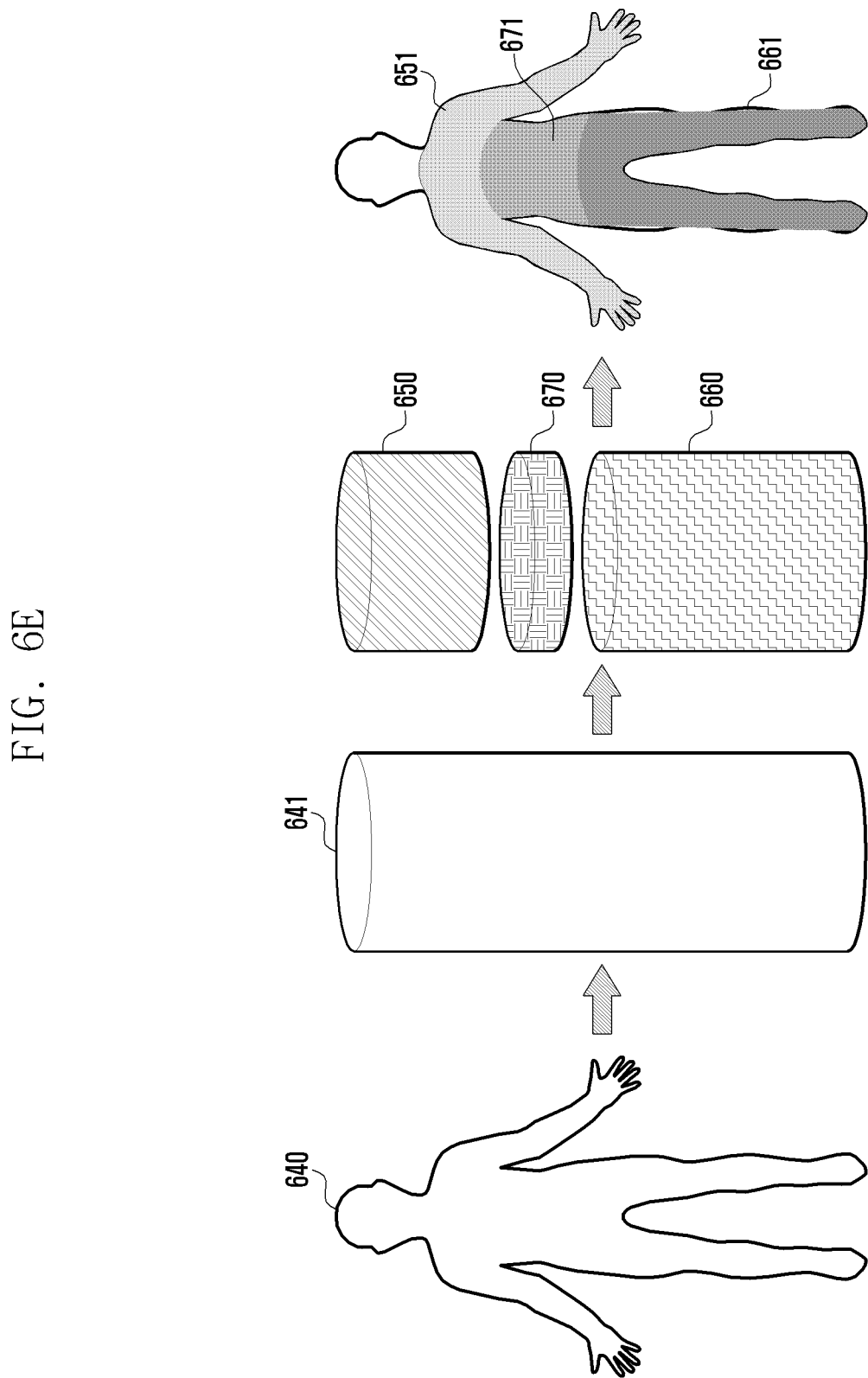
FIG. 6E illustrates a method of providing body composition information for each body part of the user according to certain embodiments of the disclosure.
Figure 6F:
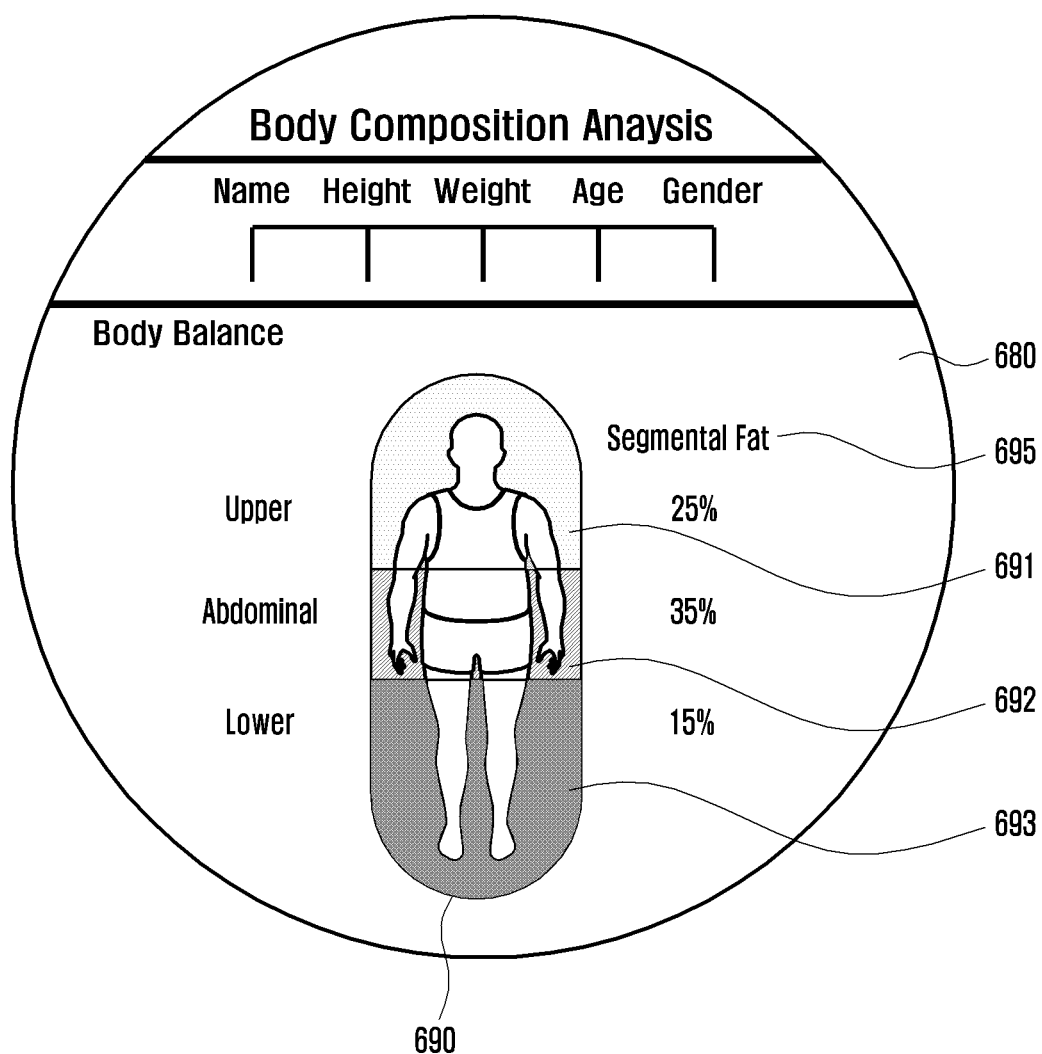
FIG. 6F illustrates that body composition for each body part of the user is displayed on a display according to certain embodiments of the disclosure.

For example, as illustrated in FIG. 6C, the first electrode 533-1 and the third electrode 533-3 may be in contact with one arm of the user, and the second electrode 533-2 and the fourth electrode 533-4 may be in contact with the other arm of the user. As illustrated in FIG. 2B, when the first electrode 533-1 and the third electrode 533-3 are disposed in some areas of the rear surface (such as, for example, the rear surface 210B of FIG. 2B) of the housing (such as, for example, the housing 210 of FIG. 2B) of the electronic device, the first electrode 533-1 and the third electrode 533-3 may come into contact with the back of the user's arm on which the electronic device is worn. As illustrated in FIGS. 2A and 2B, when the second electrode 533-2 and the fourth electrode 533-4 are disposed in some areas of the side surface (such as, for example, the side surface 210C of FIGS. 2A and 2B) of the housing of the electronic device, the second electrode 533-2 and the fourth electrode 533-4 may come into contact with fingers of the arm on which the user does not wear the electronic device. For example, second electrode 533-2 and the fourth electrode 533-4 may come into contact with the user's thumb and index finger, respectively.

As described above, the plurality of electrodes (the first electrode 533-1, the second electrode 533-2, the third electrode 533-3, and the fourth electrode 533-4) of the first sensor 530 may come into contact with both arms of the user to generate the first loop 610. Referring to FIG. 6C, the first electrode 533-1 and the second electrode 533-2 may be connected to the first alternating current generator 531. The alternating current generated by the first alternating current generator 531 may thus be transmitted to the user's body through the first electrode 533-1 or the second electrode 533-2. The third electrode 533-3 and the fourth electrode 533-4 may be connected to the first voltage measurer 532. The first voltage measurer 532 may measure a voltage according to the alternating current that is applied to the user's body through the first electrode 533-1 or the second electrode 533-2. The processor may calculate first impedance for the first part of the user's body (such as, for example, the upper body indicating an area including both arms and a portion of the trunk of the user) on the basis of the applied alternating current and the measured voltage (such as, for example, first biometric information). According to certain embodiments, as illustrated in FIGS. 6B and 6C, the first loop 610 may be generated in the first part of the user's body. The first biometric information measured through the first sensor 530 may be biometric information for the user's body, and the first impedance calculated using the first biometric information may be impedance for the user's upper body.

The human body may be divided into a fat part and a non-fat part. Mass of the non-fat part is referred to as fat-free mass (FFM). The non-fat art may be divided into water, muscle, and other parts, and component ratios of the non-fat part may be consistently maintained. For example, the amount of water may be about 73% of FFM. When the amount of fat is calculated, fat-free mass can be obtained through the weight, and component ratios of fat-free mass is fixed, and thus body composition can be obtained if the amount of fat is calculated. The amount of fat may be calculated through impedance, as per the following:

$$\text{Total body fat} = A0 + (A1 \times \text{impedance index}) + (A2 \times \text{weight}) + (A3 \times \text{weight}) + (A4 \times \text{age}) + (A5 \times \text{gender})$$

As described above, the total body fat may be calculated by the user profile such as height, weight, age, and gender, the impedance index, and the weights such as A0 to A5. Here, the impedance index may be obtained by dividing square of the height by impedance. The impedance used for calculating the impedance index may be at least one of the first impedance and the second impedance. The second impedance may be calculated by second biometric information measured by the external electronic device 400.

Weights A0 to A5 may be determined on the basis of statistical data. As described above, the user profile may be determined on the basis of the user input and the measurement value of the external electronic device 400, and the first impedance is calculated through the processor and thus the total body fat may be calculated using the first impedance and the user profile. Through the total body fat, total body fat-free mass may be obtained on the basis of difference between the user's weight and the total body fat. Since the total body fat-free mass has a constant component ratio, ratios of components included in the total body fat-free mass can be calculated. A user's total body composition may be calculated on the basis of the component ratio of the total body fat-free mass in operation 6320. The processor (such as, for example, the processor 510 of FIG. 4) may calculate total body impedance (such as, for example, total body impedance 641 of FIG. 6E) by inversely using the above equation on the basis of the total body composition in operation 6320.

According to certain embodiments, the total body fat may be calculated using impedance. For example, the total body fat may be calculated through the following equation:

$$\text{Total body fat} = B0 + (B1 \times \text{impedance}) + (B2 \times \text{weight}) + (B3 \times \text{weight}) + (B4 \times \text{age}) + (B5 \times \text{gender})$$

Here, the impedance may be the first impedance or the second impedance. Weights B0 to B5 may be determined on the basis of statistical data. Total body fat-free mass may be calculated through the weight and the total body fat. Since the total body fat-free mass has a constant component ratio, the total body composition may be calculated using the total body fat-free mass.

The processor may calculate first body composition (such as, for example, first body composition 651 of FIG. 6E) by using the first impedance in operation 6330. Since the first impedance is calculated in the first loop 610 configured in the user's upper body, the first body composition calculated using the first impedance may be body composition of the user's upper body.

The second sensor 430 of the external electronic device 400 may measure second biometric information. Referring to FIG. 6B, the second sensor 430 may be in contact with the second part of the user's body (such as, for example, the lower body including an area including both legs and a portion of the trunk of the user) to generate the second loop 630. For example, as illustrated in FIG. 6D, the fifth electrode 433-1 and the seventh electrode 433-3 may be in contact with one sole of the user, and the sixth electrode 433-2 and the eighth electrode 433-4 may be in contact with the other sole of the user. The second biometric information may be information utilized to calculate the second impedance (such as, for example, the second impedance 660 of FIG. 6E). For example, the second biometric information may be information related to an alternating current, an alternating voltage, and an alternating frequency.

As described above, a plurality of electrodes (the fifth electrode 433-1, the sixth electrode 433-2, the seventh electrode 433-3, and the eighth electrode 433-4) of the second sensor 430 may come into contact both soles of the user to generate the second loop 630. Referring to FIG. 6D, the fifth electrode 433-1 and the sixth electrode 433-2 may be connected to the second alternating current generator 431. The alternating current generated by the second alternating current generator 431 may be applied to the user's body through the fifth electrode 433-1 or the sixth electrode 433-2. The sixth electrode 433-2 and the eighth electrode 433-4 may be connected to the second voltage measurer 432. The second voltage measurer 432 may measure a voltage according to the alternating current applied to the user's body through the sixth electrode 433-2 or the eighth electrode 433-4. The processor may calculate the second impedance for the second part of the user's body on the basis of the applied alternating current and the measured voltage (such as, for example, the second biometric information). According to certain embodiments, as illustrated in FIGS. 6B and 6D, the second loop 630 may be generated in the second part of the user's body. The second biometric information measured through the second sensor 430 may be biometric information for the user's lower body, and the second impedance calculated using the second biometric information may be impedance for the user's lower body.

The electronic device may receive the second biometric information measured by the external electronic device 400 in operation 6340. The processor of the electronic device may calculate the second impedance on the basis of the second biometric information. The processor may calculate second body composition (such as, for example, second body composition 661 of FIG. 6E) by using the second impedance in operation 6350. Since the second impedance is calculated using the second biometric information measured in the second loop 630 configured in the user's lower body, the second body composition calculated using the second impedance may be body composition of the user's lower body.

According to certain embodiments, the processor may calculate third impedance (such as, for example, third impedance 670 of FIG. 6E) for a third part of the body on the basis of the total body impedance, the first impedance, and the second impedance in operation 6360. The third part of the body may be a part distinguished from the first part and the second part. The third part may be, for example, an abdomen except for the upper body and the lower body. The third impedance may be calculated on the basis of difference between the total body impedance and a sum of the first impedance and the second impedance.

Referring to FIG. 6E, the total body impedance 641 may be obtained from the user's total body composition 640. Since a sum of the first impedance 650, the second impedance 660, and the third impedance 670 is the total body impedance 641, the third impedance 670 may be obtained from the total body impedance 641, the first impedance 650, and the second impedance 660. The first impedance 650 is impedance related to the user's upper body obtained through the first loop 610 configured in the user's upper body and the second impedance 660 is impedance related to the user's lower body obtained through the second loop 630 configured in the user's lower body, and thus the third impedance 670 may be impedance related to the abdomen except for the upper body and the lower body from the user's whole body. The processor may calculate third body composition 671 by using the third impedance 670 in operation 6370. As described above, since the third impedance 670 is the impedance related to the user's abdomen, the third body composition 672 may be a user's abdomen body composition.

The first body composition 651 calculated on the basis of the first impedance 650 may be body composition for the user's upper body, the second body composition 661 calculated on the basis of the second impedance 660 may be body composition for the user's lower body, and the third body composition 671 calculated on the basis of the third impedance 670 may be body composition for the user's abdomen.

According to certain embodiments, the processor (such as, for example, the processor 510 of FIG. 4) may display the total body composition, the first body composition, the second body composition, or the third body composition on a display 680 (such as, for example, the display device 160 of FIG. 1) in operation 6380. For example, as illustrated in FIG. 6F, a human body 690 may be graphically divided into three parts, including a first part 691, a second part 692, and a third part 693, and body composition information of the user may be displayed on a display 680 in such a manner that information for the first body composition, second body composition, or third body composition matches each part. The first part 691 includes an upper body part, and thus information related to the first body composition (such as, for example, the first body composition 651 of FIG. 6E) corresponding to body composition related to the upper body may be displayed in the first part 691. The third part 693 includes a lower body, and thus information related to the second body composition (such as, for example, the second body composition 661 of FIG. 6E) corresponding to body composition related to the lower body may be displayed in the third part 693. The second part 692 includes an abdomen part, and thus information related to the third body composition (such as, for example, the third body composition 671 of FIG. 6E) corresponding to body composition related to the abdomen may be displayed in the second part 692. The body composition information may be hierarchically displayed. For example, segmental fat 695 of each part may be first displayed in each part, and when the user touches each part, detailed body composition information for each part may be displayed. The body composition includes muscles, water, and minerals, and thus the processor may also display muscles, water, and minerals on the display as well as the segmental fat 695. In addition, the body composition information for each part may be displayed on the display 680 in various forms.

As described above, the processor of the electronic device according to certain embodiments of the disclosure may calculate biometric and total body composition on the basis of the value measured by the first sensor 530 of the electronic device and calculate body composition of the lower body on the basis of the value measured by the second sensor 430 of the external electronic device 400, so as to calculate body composition of the abdomen. Accordingly, the user may conveniently identify and manage body composition for each body part.

Figure 7B:
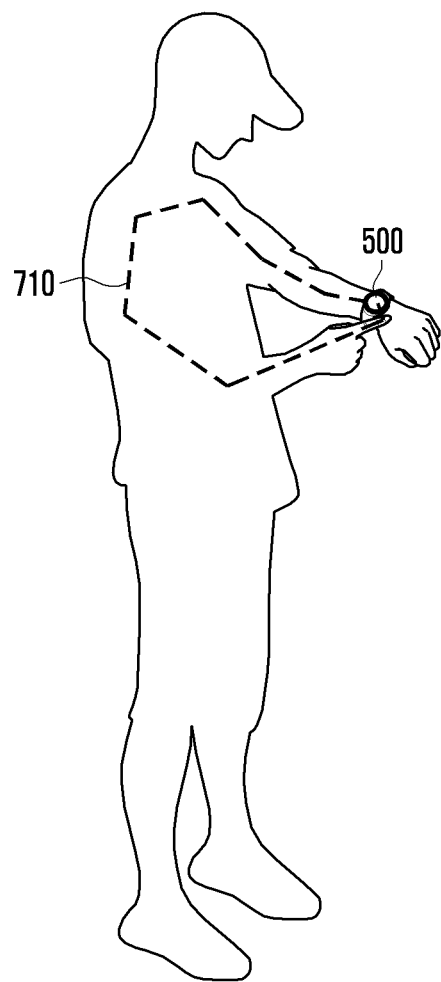
FIGS. 7B and 7C illustrate an electronic device to generate electric loops in a user's body part according to certain embodiments of the disclosure.
Figure 7C:
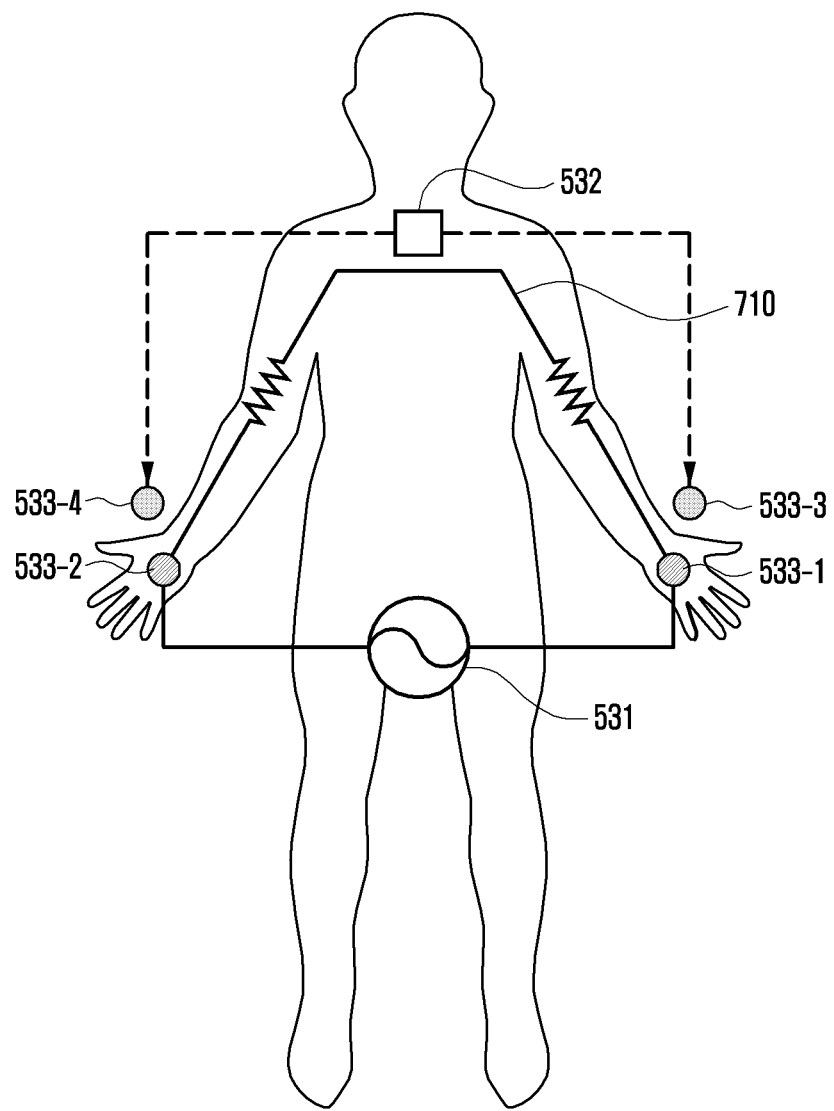
Figure 7E:
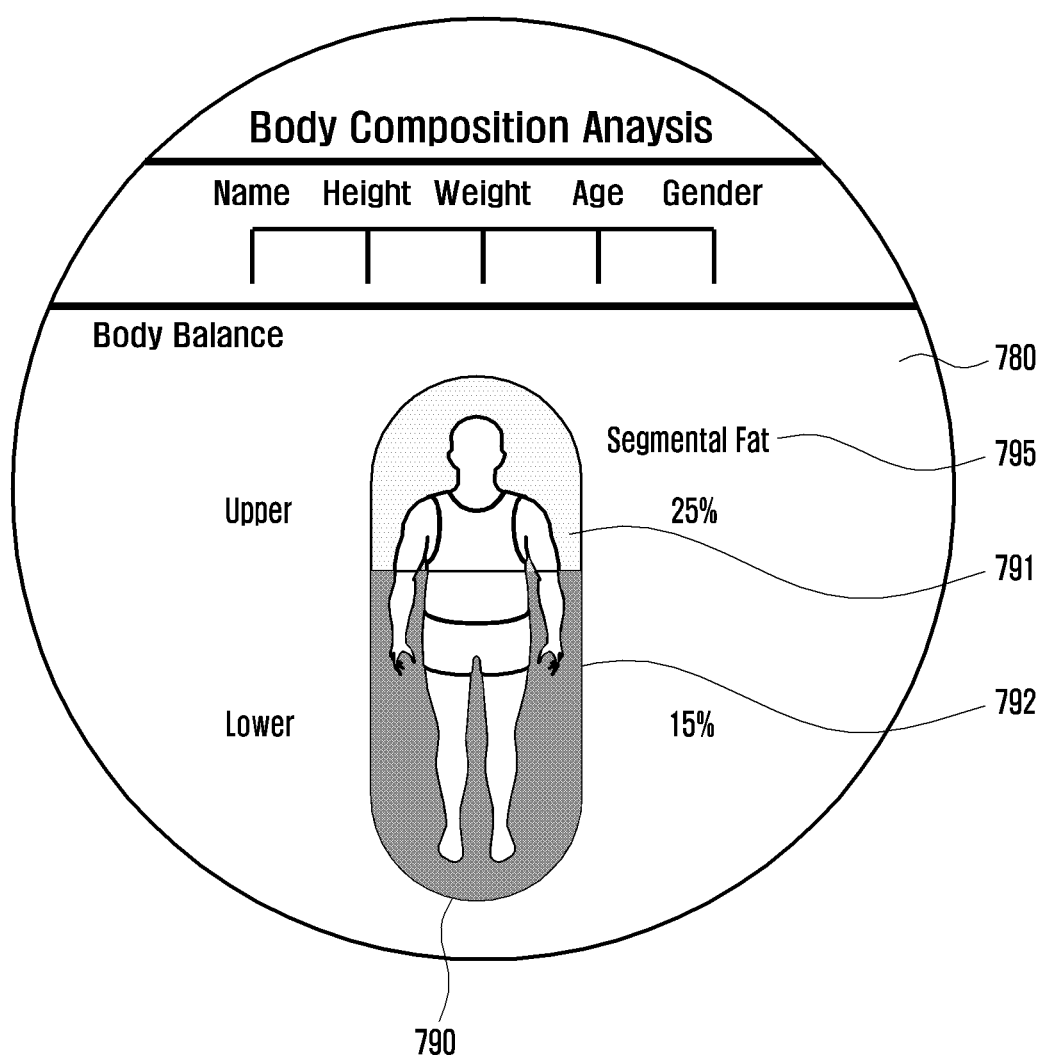
FIG. 7E illustrates that body composition for each body part of the user is displayed on the display according to certain embodiments of the disclosure.

Subsequently, the second scenario in which the electronic device and the external electronic device 400 are not connected is described. FIGS. 7B and 7C illustrate an electronic device to generate electrical loops in a user's body part according to certain embodiments of the disclosure, FIG. 7D illustrates a method of providing body composition information for each body part of the user according to certain embodiments of the disclosure, and FIG. 7E illustrates that body composition for each body part of the user is displayed on a display according to certain embodiments of the disclosure.

The first sensor 530 of the electronic device 500 may measure first biometric information (such as, for example, first biometric information 750 of FIG. 7D) in operation 6410. Referring to FIG. 7B, the first sensor (such as, for example, the first sensor 530 of FIG. 5) of the electronic device 500 may be in contact with a first part (such as, for example, an upper body) of the user's body and generate a first loop 710. For example, as illustrated in FIG. 7C, the first electrode 533-1 and the third electrode 533-3 may be in contact with one arm of the user, and the second electrode 533-2 and the fourth electrode 533-4 may be in contact with the other arm of the user. As illustrated in FIG. 2B, when the first electrode 533-1 and the third electrode 533-3 are disposed in some areas of the rear surface (such as, for example, the rear surface 210B of FIG. 2B) of the housing (such as, for example, the housing 210 of FIG. 2B) of the electronic device, the first electrode 533-1 and the third electrode 533-3 may come into contact with As illustrated in FIGS. 2A and 2B, when the second electrode 533-2 and the fourth electrode 533-4 are disposed in some areas of the side surface (such as, for example, the side surface 210C of FIGS. 2A and 2B) of the housing of the electronic device, the second electrode 533-2 and the fourth electrode 533-4 may come into contact with fingers of the arm on which the user does not wear the electronic device. For example, the second electrode 533-2 and the fourth electrode 533-4 may come into contact with the user's thumb and index finger, respectively.

As described above, the plurality of electrodes (the first electrode 533-1, the second electrode 533-2, the third electrode 533-3, and the fourth electrode 533-4) of the first sensor 530 may come into contact with both arms of the user to generate the first loop 710. Referring to FIG. 7C, the first electrode 533-1 and the second electrode 533-2 may be connected to the first alternating current generator 531. The alternating current generated by the first alternating current generator 531 may be applied to the user's body through the first electrode 533-1 or the second electrode 533-2. The third electrode 533-3 and the fourth electrode 533-4 may be connected to the first voltage measurer 532. The first voltage measurer 532 may measure a voltage according to the alternating current applied to the user's body through the first electrode 533-1 or the second electrode 533-2. A processor (such as, for example, the processor 510 of FIG. 4) may calculate first impedance for the first part of the user's body on the basis of the applied alternating current and the measured voltage (such as, for example, the first biometric information). According to certain embodiments, as illustrated in FIG. 7C, the first loop 710 may be generated in the upper body of the user's body (such as, for example, an area including both arms and a portion of the trunk of the user). The first biometric information measured through the first sensor 530 may be biometric information for the user's upper body, and first impedance calculated using the first biometric information may be impedance for the user's upper body.

$$\text{Total body fat} = A0 + (A1 \times \text{impedance index}) + (A2 \times \text{weight}) + (A3 \times \text{weight}) + (A4 \times \text{age}) + (A5 \times \text{gender})$$

As described above, the total body fat may be calculated by the user profile such as height, weight, age, and gender, the impedance index, and the weights such as A0 to A5. Here, the impedance index may be obtained by dividing square of the height by impedance. The impedance for calculating the impedance index may be the first impedance or the second impedance.

Weights A0 to A5 may be determined on the basis of statistical data. As described above, the user profile may be determined on the basis of a user input and a measurement value of the external electronic device 400 and the first impedance is obtained through the first biometric information measured by the first sensor 530, and thus the total body fat may be acquired through the first impedance and the user profile. Through the total body fat, total body fat-free mass may be obtained on the basis of difference between the user's weight and the total body fat. Since the total body fat-free mass has a constant component ratio, ratios of components included in the total body fat-free mass can be calculated. Total body composition of the user may be calculated on the basis of the total body fat and component ratios of the total body fat-free mass in operation 6420. The processor may calculate total body impedance (such as, for example, total body impedance 741 of FIG. 7D) by using the total body composition in operation 6420.

According to certain embodiments, the total body fat may be calculated using impedance. For example, the total body fat may be calculated through the following equation:

$$\text{Total body fat} = B0 + (B1 \times \text{impedance}) + (B2 \times \text{weight}) + (B3 \times \text{weight}) + (B4 \times \text{age}) + (B5 \times \text{gender})$$

Here, the impedance may be the first impedance or the second impedance. Weights B0 to B5 may be determined on the basis of statistical data. Total body fat-free mass may be calculated through the weight and the total body fat. Since the total body fat-free mass has a constant component ratio, the total body composition may be calculated using the total body fat-free mass.

The processor may calculate first body composition (such as, for example, first body composition 751 of FIG. 7D) by using the first impedance in operation 6430. Since the first impedance is calculated in the first loop 710 created in the user's upper body, the first body composition calculated using the first impedance may reflect the body composition of the user's upper body.

According to certain embodiments, the processor may calculate a fourth impedance (such as, for example, fourth impedance 760 of FIG. 7D) by using the total body impedance and the first impedance. The fourth impedance may be calculated as difference between the total body impedance and the first impedance. As described above, since the first impedance is the impedance related to the upper body of the user, the fourth impedance calculated as the difference between the total body impedance and the first impedance may be impedance related to a part except for the upper body. The processor may calculate fourth body composition (such as, for example, fourth composition 761 of FIG. 7D) by using the fourth impedance. The fourth body composition may be body composition of the part except for the upper body of the user.

Referring to FIG. 7D, the processor may calculate total body impedance 741 on the basis of the total body composition 740 of the user. Since a sum of the first impedance 750 and the fourth impedance 760 is the total body impedance 741, the fourth impedance 760 may be obtained from the total body impedance 741 and the first impedance 750. The first impedance 750 is impedance related to the upper body of the user calculated through the first loop 710 configured in the upper body of the user, and thus the fourth impedance 760 may be impedance related to the part except for the upper body of the user's whole body. The processor may calculate fourth body composition 761 by using the fourth impedance 760. As described above, since the fourth impedance 760 is impedance related to the part except for the upper body of the user, the fourth body composition 761 may be body composition of the part except for the upper body of the user.

The first body composition 751 calculated by the processor on the basis of the first impedance 750 may be body composition for the upper body of the user, and the fourth body composition 761 calculated by the fourth impedance 760 by the processor may be body composition for the part except for the abdomen of the user.

According to certain embodiments, the processor (such as, for example, the processor 510 of FIG. 4) may display at least one of the total body composition, the first body composition, or the fourth body composition on the display 780 (such as, for example, the display device 160 of FIG. 1) in operation 6440. For example, as illustrated in FIG. 7E, a human body 790 may be divided into two parts (i.e., a first part 791 and a second part 792) and a user's body composition information may be displayed on the display 780 in such a manner that the first body composition and the fourth body composition match the respective two parts. The first part 791 may be the upper body portion, and thus information related to first body composition (such as, for example, the first body composition 751 of FIG. 7D) corresponding to the body composition related to the upper body may be displayed in the first part 791. The second part 793 may be a portion of the body excepting the upper body, and thus information related to fourth body composition (such as, for example, the fourth body composition 761 of FIG. 7D) may be displayed in the third part 793. The body composition may be hierarchically displayed. For example, the amount of fat 795 of each part may be first displayed in each part, and when the user touches each part, detailed body composition information for each part may be displayed. The body composition includes muscles, water, and minerals, and thus the processor may also display muscles, water, and minerals on the display as well as the amount of fat 795. In addition, the body composition information for each part may be displayed on the display 780 in various forms.

Figure 8A:
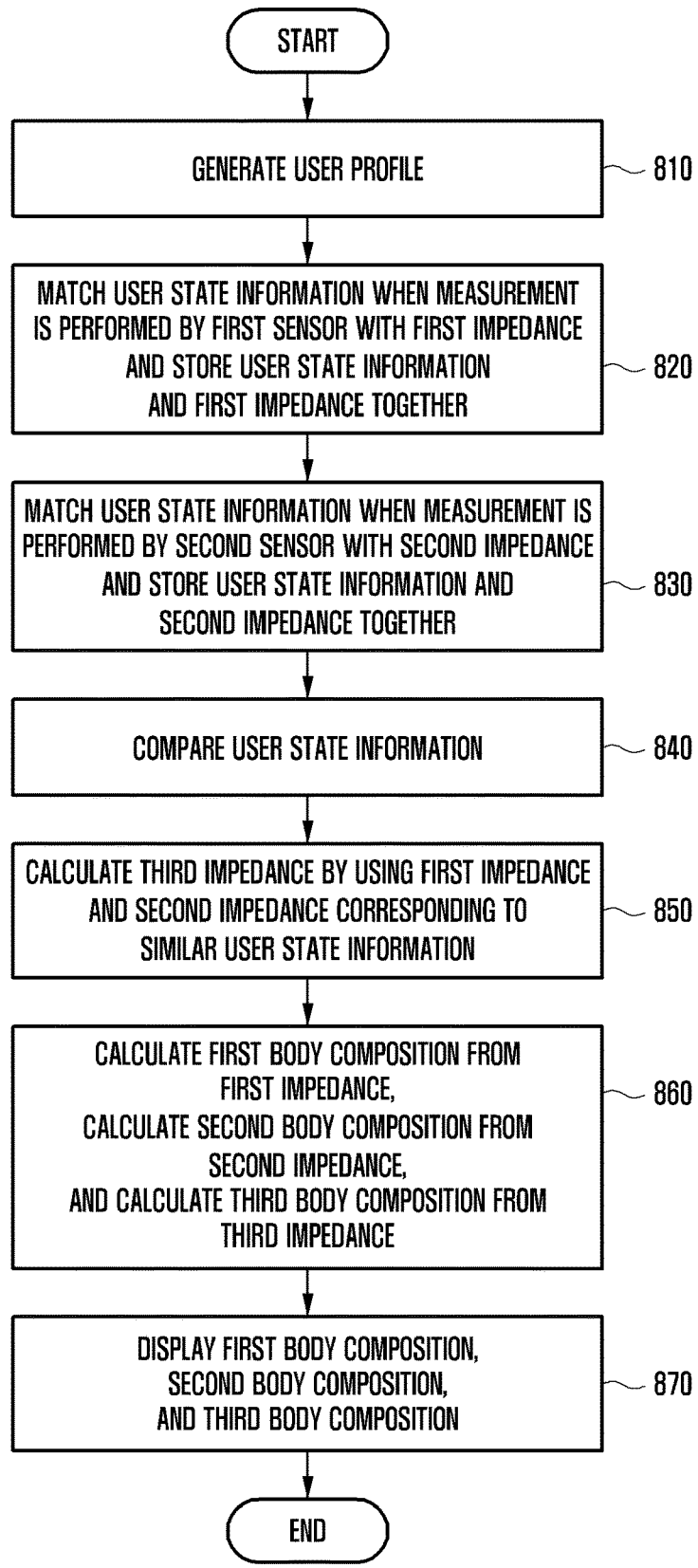
FIG. 8A is a flowchart illustrating a method of providing body composition information according to certain embodiments of the disclosure.
Figure 8B:
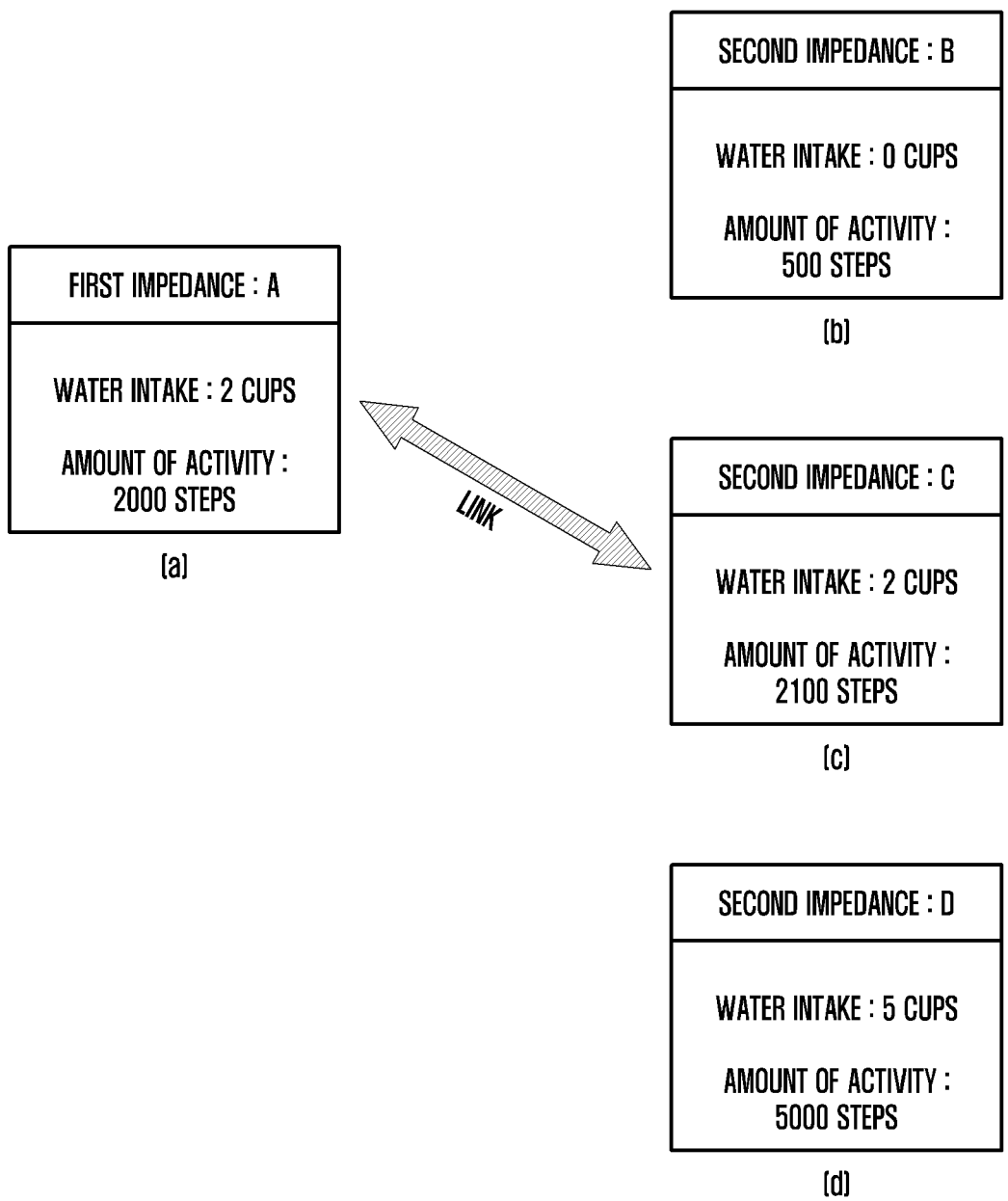
FIG. 8B illustrates impedance information linked to user state information according to certain embodiments of the disclosure.

FIG. 8A is a flowchart illustrating a body composition provision method according to certain embodiments of the disclosure, and FIG. 8B illustrates impedance information linked to a user's state information according to certain embodiments of the disclosure. The flowchart illustrated in FIG. 8A is only one example, and orders of the respective operations may be variously changed.

According to certain embodiments, the processor (such as, for example, the processor 510 of FIG. 4) may calculate body composition by linking impedance calculated at different time points by the electronic device (such as, for example, the electronic device 500 of FIG. 4) and the external electronic device (such as, for example, the external electronic device 400 of FIG. 4).

According to certain embodiments, the processor may calculate third impedance corresponding to impedance related to the abdomen by linking the first impedance calculated using the first biometric information measured by the first sensor (such as, for example, the first sensor 530 of FIG. 4) of the electronic device and the second impedance calculated using the second biometric information measured by the second sensor (such as, for example, the second sensor 430 of FIG. 4) of the external electronic device at a time point that is the closest to the time point at which the first biometric information is measured.

According to certain embodiments, the processor (such as, for example, the processor 510 of FIG. 4) of the electronic device may display an interface capable of receiving an input of a user profile on the display of the electronic device so that the user can input the user profile including his/her own weight, age, gender, and height into the electronic device. The electronic device may generate a user profile on the basis of a user input in operation 810. When the external electronic device can measure the user's weight while the electronic device receives the input of the user profile from the user, the electronic device may receive the user's weight from the external electronic device and store the same in the user profile.

According to certain embodiments, the processor may calculate body composition by linking impedance measured at different time points on the basis of the user state information. The user state information may be information including water intake and the amount of activity of the user (such as, for example, step count and exercise time). The water intake may be information input by the user. The amount of activity may be information stored by the sensor according to user's activities. The measurement of body composition through impedance may be influenced by the water intake and the amount of activity of the user. If body composition is calculated by linking impedance measured at time points at which there are similar water intake and amounts of activity, body composition for each body part of the user may be calculated by linking impedance measured at different time points. According to certain embodiments, the processor of the electronic device may match user state information with the first impedance at a time point at which the first biometric information is measured by the first sensor 530 and store the user state information and the first impedance together as illustrated in FIG. 8B, element [a] in operation 820. Further, the processor may match user state information with the second impedance at a time point at which the second biometric information is measured by the second sensor 430 of the external electronic device 400 and store the user state information and the second impedance together as illustrated in FIG. 8B, elements [b], [c] and [d] in operation 830.

According to certain embodiments, the processor may compare the user state information matching the first impedance (such as, for example, FIG. 8B, element [a] and the user state information matching the second impedance (such as, for example, FIG. 8B, elements [b], [c] and [d]) in operation 840. The processor may determine similarity between user state information. The determination of similarity between user state information may be performed in various methods. For example, numerical values included in user state information may be compared, and when the comparison result is equal to or lower than a preset difference, it may be determined that the user state information is similar. When there are many pieces of user state information determined to be similar, impedances having the closest measurement point time may be linked. In another example, impedances having the smallest difference between numerical values included in user state information may be linked. In comparison between FIG. 8B, element [a] and FIG. 8B, elements [b], [c], and [d], the numerical values in user state information of FIG. 8B, element [a] and FIG. 8B, element [c] are the most similar, and thus the processor may calculate third impedance by linking first impedance (A) of FIG. 8B, element [a] and second impedance (C) of FIG. 8B, element [c] in operation 850.

According to certain embodiments, as described above in the first scenario, the processor may calculate the first body composition and the total body composition from the first impedance, calculate the second body composition from the second impedance, and calculate the third body composition from the third impedance in operation 860. The processor may display the calculated body composition information in operation 870.

According to certain embodiments, the electronic device may store the first impedance in the server and the external electronic device may store the second impedance in the server. The electronic device may calculate the first body composition, the second body composition, and the third body composition on the basis of the first impedance and the second impedance stored in the server. The electronic device may calculate the first body composition, the second body composition, and the third body composition by using the first impedance calculated using the measured first biometric information and the second impedance stored in the server.

Although it has been described that the total body composition is calculated from the first impedance, the total body composition can be calculated from the second impedance.

Further, it has been described above that the processor calculates the total body impedance, calculates the third impedance by using the total body impedance, the first impedance, and the second impedance, and calculates the third body composition on the basis of the third impedance, the processor can calculate the third body composition by using the total body composition, the first body composition, and the second body composition. For example, it is also possible to determine the difference between the total body composition and the sum of the first body composition and the second body composition as the third body composition.

According to certain embodiments, the first alternating current generator (the first alternating current generator 531 of FIG. 1) of the first sensor (such as, for example, the first sensor 530 of FIG. 4) and the second alternating current generator (such as, for example, the second alternating current generator 431 of FIG. 4) of the second sensor (such as, for example, the second sensor 430 of FIG. 4) may generate alternating currents having different frequencies to make a first loop and a second loop. The degree of penetration of the alternating current for each body part may vary depending on the frequency of the alternating current. For example, the alternating current having a frequency of 50 kHz has low permeability to cell membrane. Accordingly, the alternating current of 50 kHz can be considered to measure extracellular water (ECW). Unlike this, the alternating current having a frequency equal to or lower than 1 mHz has high permeability to cell membrane and thus can be considered to measure even intercellular water (ICW). As described above, when different frequencies are used, extracellular water and intercellular water can be distinguished, which makes more accurate measurement of body composition possible.

An electronic device according to certain embodiments of the disclosure may include a display, a first sensor configured to measure first biometric information for a first part of a body of a user, a communication module, and a processor operatively connected to the display, the first sensor, and the communication module, and the processor may be configured to calculate a first impedance by using the first biometric information and calculate a first body composition, based on the first impedance, receive second biometric information from an external electronic device including a second sensor configured to measure the second biometric information for a second part of the body of the user through the communication module, calculate a second impedance by using the second biometric information and calculate a second body composition, based the second impedance, calculate a total body composition, based on at least one of the first impedance and the second impedance, calculate a third body composition for a third part of the body of the user, based on the total body composition, the first body composition, and the second body composition, and display at least one of the total body composition, the first body composition, and the second body composition, and the third body composition on the display.

The processor may be configured to calculate a total body impedance from the total body composition, calculate a third impedance, based on the total body impedance, the first impedance, and the second impedance, and calculate the third body composition from the third impedance.

The first sensor may include a plurality of electrodes to measure the first biometric information.

The first sensor may include a first electrode and a second electrode disposed on a rear surface facing the display of the electronic device and a third electrode and a fourth electrode disposed on a side surface of the electronic device.

The processor may be configured to determine a difference between the total body impedance and a sum of the first impedance and the second impedance as the third impedance.

The processor may be configured to generate a user profile including at least one of a user's weight, age, gender, and height, based on a user input, and calculate the total body composition, based on the user profile and the first impedance.

The processor may be configured to allow the first sensor to measure first biometric information for each frequency by applying alternating currents having different frequencies which penetrate different parts of the body and calculate the first body composition, based on the measured first biometric information.

The processor may be configured to store user state information including water intake and an amount of activity of the user, based on a user input, match user state information at a time point at which the first biometric information is measured and the first impedance and store the user state information and the first impedance together, match user state information at a time point at which the second biometric information is measured and the second impedance and store the user state information and the second impedance together, and calculate the third impedance by using the first impedance and the second impedance selected based on the user state information matching the first impedance and the second impedance.

The processor may be configured to calculate third impedance, based on first impedance and second impedance calculated using first biometric information and second biometric information measured at the closest time point, based on time points at which the first biometric information and the second biometric information are measured.

A method of providing body composition information of a user through an electronic device according to certain embodiments disclosed in the document may include an operation of measuring first biometric information for a first part of a body of a user through a first sensor, an operation of calculating a first impedance by using the first biometric information and calculating a first body composition, based on the first impedance, an operation of receiving second biometric information from an external electronic device including a second sensor configured to measure second biometric information for a second part of the body of the user, an operation of calculating a second impedance by using the second biometric information and calculating a second body composition, based on the second impedance, an operation of calculating a total body composition, based on at least one of the first impedance and the second impedance, an operation of calculating a third body composition for a third part of the body of the user, based on the total body composition, the first body composition, and the second body composition, and an operation of displaying at least one of the total body composition, the first body composition, the second body composition, and the third body composition on a display.

The operation of calculating the third body composition may include an operation of calculating a total body impedance from the total body composition, an operation of calculating a third impedance, based on the total body impedance, the first impedance, and the second impedance, and an operation of calculating the third body composition from the third impedance.

The first sensor may include a plurality of electrodes to measure the first biometric information.

The first sensor may include a first electrode and a second electrode disposed on a rear surface facing the display of the electronic device and a third electrode and a fourth electrode disposed on a side surface of the electronic device.

The third impedance may be determined as a difference between the total body impedance and a sum of the first impedance and the second impedance.

The method may further include an operation of generating a user profile including at least one of a user's weight, age, gender, and height, and the operation of calculating the total body composition may be an operation of calculating the total body composition, based on the user profile and the first impedance.

The operation of measuring the first biometric information through the first sensor may be an operation of allowing the first sensor to measure first biometric information for each frequency by applying alternating currents having different frequencies which penetrate different parts of the body.

The method may further include an operation of storing user state information including water intake and an amount of activity of the user, an operation of matching user state information at a time point at which the first biometric information is measured and the first impedance and storing the user state information and the first impedance together, and an operation of matching user state information at a time point at which the second biometric information is measured and the second impedance and storing the user state information and the second impedance together, and the operation of calculating the third body composition may be an operation of calculating the third impedance by using the first impedance and the second impedance selected based on the user state information matching the first impedance and the second impedance.

The operation of calculating the third body composition may be an operation of calculating a third impedance, based on the first impedance and the second impedance calculated using first biometric information and second biometric information measured at the closest time point, based on time points at which the first biometric information and the second biometric information are measured.

An electronic device according to certain embodiments of the disclosure may include a display, a first sensor configured to measure first biometric information between both arms of a user, a communication module, and a processor operatively connected to the display, the first sensor, and the communication module, and the processor may be configured to identify whether the electronic device is linked to an external electronic device including a second sensor configured to measure second biometric information between both legs of the user and determine to operate in one scenario among a plurality of scenarios, based on whether the electronic devices are linked, and a first scenario of the plurality of scenarios is a scenario in which the processor is configured to calculate a first impedance by using the first biometric information, calculate a first body composition, based on the first impedance, receive second biometric information from the external electronic device through the communication module, calculate a second impedance by using the second biometric information, calculate a second body composition from the second impedance, calculate a total body composition, based on at least one of the first impedance and the second impedance, calculate a third body composition for a third part of a body of the user, based on the total body composition, the first body composition, and the second body composition, and display at least one of the total body composition, the first body composition, the second body composition, and the third body composition on the display and a second scenario of the plurality of scenarios is a scenario in which the processor is configured to calculate the first impedance by using the first biometric information, calculate the first body composition, based on the first impedance, calculate the total body impedance and the total body composition from the first impedance, and display at least one of the total body composition and the first body composition on the display.

The processor may be configured to calculate the total body impedance from the total body composition, calculate a third impedance, based on the total body impedance, the first impedance, and the second impedance, and calculate the third body composition from the third impedance in the first scenario.

The embodiments according to the disclosure in the specification and drawings merely present specific examples to easily describe the technical content according to the embodiments of the disclosure and help understanding of the embodiments of the disclosure but do not limit the scope of the embodiments of the disclosure. Therefore, the scope of certain embodiments of the disclosure should be construed such that not only the embodiments disclosed herein but also all changed or modified forms derived on the basis of the technical idea of certain embodiments of the disclosure should be included in the scope of the certain embodiments of the disclosure.

What is claimed is:

1. An electronic device, comprising:
a display;
a first sensor configured to measure first biometric information for a first part of a body of a user;
a communication module; and
a processor operatively connected to the display, the first sensor, and the communication module,
wherein the processor is configured to:
obtain a first impedance via the first biometric information, and obtain a first body composition based on the first impedance,
receive second biometric information for a second part of the body of the user from an external electronic device including a second sensor via the communication module, the second biometric information being obtained via the second sensor,
identify a second impedance using the second biometric information,
obtain a total body composition, based at least on the first impedance and the second impedance,
calculate a third body composition for a third part of the body of the user in absence of a third sensor, based on the total body composition, the first body composition, and the second body composition, and
display at least one of the total body composition, the first body composition, and the second body composition, and the third body composition on the display.

2. The electronic device of claim 1, wherein the processor is further configured to:
obtain a total body impedance from the total body composition,
obtain a third impedance, based on the total body impedance, the first impedance, and the second impedance, and
obtain a third body composition based on the third impedance.

3. The electronic device of claim 2, wherein the processor is further configured to:
determine a difference between the total body impedance, and a sum of the first impedance and the second impedance as the third impedance.

4. The electronic device of claim 2, wherein the processor is further configured to:
store user state history over time, including a water intake amount, and an amount of physical activity of the user,
store a first impedance history over first impedance values over time, and a second impedance history of second impedance values over time, match, based on a first time point at which the first biometric information is measured, first values of the user state history with first impedance values from the first impedance history, and store the first values of the user state history and the first impedance values together,
match, based on a second time point at which the second biometric information is measured, second values of the user state history with second impedance values from the second impedance history, and store the second values of the user state history and the second impedance values together, and
obtain a third impedance using the first impedance values and the second impedance values.

5. The electronic device of claim 1, wherein the first sensor includes a plurality of electrodes for measuring the first biometric information.

6. The electronic device of claim 5, wherein the plurality of electrodes of the first sensor includes a first electrode and a second electrode disposed on a rear surface opposite the display of the electronic device, and a third electrode and a fourth electrode disposed on a side surface of the electronic device.

7. The electronic device of claim 1, wherein the processor is further configured to:
generate a user profile including at least one of a user's weight, age, gender, and height, based on a user input, and
wherein obtaining the total body composition is based at least on the user profile and the first impedance.

8. The electronic device of claim 1, wherein the processor is further configured to:
control the first sensor to measure the first biometric information for each of a plurality of frequencies by applying alternating current having different frequencies for penetrating different parts of the body,
wherein the first body composition is obtained based on the measured first biometric information for each of the plurality of frequencies.

9. The electronic device of claim 1, wherein the processor is further configured to:
obtain a third impedance based on the first impedance and the second impedance,
wherein the first and second impedances are obtained using values of the first biometric information and the second biometric information that are matched with each other based on proximity of time of measurement.

10. A method of providing body composition information through an electronic device, the method comprising:
measuring first biometric information for a first part of a body of a user via a first sensor;
obtaining, via a processor, a first impedance using the first biometric information, and obtaining a first body composition based on the first impedance;
receiving, via communication circuitry, second biometric information for a second part of the body of the user from an external electronic device including a second;
identifying a second impedance using the second biometric information;
obtaining a total body composition, based at least on the first impedance and the second impedance,
calculate a third body composition for a third part of the body of the user in absence of a third sensor, based on the total body composition, the first body composition, and the second body composition, and
display at least one of the total body composition, the first body composition, and the second body composition, and the third body composition on the display.

11. The method of claim 10, further comprising:
obtaining a total body impedance from the total body composition, and
obtaining a third impedance, based on the total body impedance, the first impedance, and the second impedance,
obtaining the third body composition based on the third impedance.

12. The method of claim 11, further comprising:
determining a difference between the total body impedance, and a sum of the first impedance and the second impedance as the third impedance.

13. The method of claim 11, further comprising:
generating a user profile including at least one of a user's weight, age, gender, and height, based on a user input,
wherein obtaining the total body composition is based at least on the user profile and the first impedance.

14. The method of claim 11, further comprising:
controlling the first sensor to measure the first biometric information for each of a plurality of frequencies by applying alternating current having different frequencies for penetrating different parts of the body,
wherein the first body composition is obtained based on the measured first biometric information for each of the plurality of frequencies.

15. The method of claim 11, further comprising:
obtaining a third impedance based on the first impedance and the second impedance,
wherein the first and second impedances are obtained using values of the first biometric information and the second biometric information that are matched with each other based on proximity of time of measurement.

16. The method of claim 10, wherein the first sensor comprises a first electrode and a second electrode disposed on a rear surface opposite the display of the electronic device, and a third electrode and a fourth electrode disposed on a side surface of the electronic device.

17. The method of claim 16, further comprising:
storing user state history over time, including a water intake amount, and an amount of physical activity of the user,
storing a first impedance history over first impedance values over time, and a second impedance history of second impedance values over time; match, based on a first time point at which the first biometric information is measured, first values of the user state history with first impedance values from the first impedance history, and store the first values of the user state history and the first impedance values together,
matching, based on a second time point at which the second biometric information is measured, second values of the user state history with second impedance values from the second impedance history, and store the second values of the user state history and the second impedance values together, and
obtaining a third impedance using the first impedance values and the second impedance values.

18. An electronic device, comprising:
a display;
a first sensor configured to measure first biometric information from both arms of a user;
a communication module; and
a processor operatively connected to the display, the first sensor, and the communication module,
wherein the processor is configured to:
identify whether the electronic device is communicably linked to an external electronic device including a second sensor for measuring second biometric information from both legs of the user,
selectively activate an operational scenario from among a plurality of scenarios, based on whether the electronic devices are communicably linked,
wherein a first scenario of the plurality of scenarios causes the processor to: obtain a first impedance by using the first biometric information, obtain a first body composition, based on the first impedance, receive second biometric information from the external electronic device through the communication module, identify a second impedance by using the second biometric information, obtain a total body composition, based at least on the first impedance and the second impedance, and calculate a third body composition for a third part of the body of the user in absence of a third sensor, based on the total body composition, the first body composition, and the second body composition, and display at least one of the total body composition, the first body composition, and the second body composition, and the third body composition on the display, and
wherein a second scenario of the plurality of scenarios causes the processor to:
obtain the first impedance by using the first biometric information, obtain the first body composition, based on the first impedance, obtain a total body impedance and the total body composition from the first impedance.

19. The electronic device of claim 18, wherein the processor is further configured to:

obtain the total body impedance from the total body composition, obtain a third impedance, based on the total body impedance, the first impedance, and the second impedance, and obtain a third body composition based on the third impedance in the first scenario.

\* \* \* \* \*